(12) United States Patent
Tomita et al.

(10) Patent No.: US 8,754,048 B2
(45) Date of Patent: Jun. 17, 2014

(54) LIGHT-RECEIVING CHANNEL RHODOPSIN HAVING IMPROVED EXPRESSION EFFICIENCY

(75) Inventors: Hiroshi Tomita, Miyagi (JP); Eriko Sugano, Miyagi (JP)

(73) Assignee: Tohoku University, Sendai-Shi, Miyagi (JP)

( * ) Notice: Subject to any disclaimer, the term of this patent is extended or adjusted under 35 U.S.C. 154(b) by 0 days.

(21) Appl. No.: 13/389,755

(22) PCT Filed: Aug. 10, 2010

(86) PCT No.: PCT/JP2010/063786
§ 371 (c)(1),
(2), (4) Date: Feb. 9, 2012

(87) PCT Pub. No.: WO2011/019081
PCT Pub. Date: Feb. 17, 2011

(65) Prior Publication Data
US 2012/0190629 A1 Jul. 26, 2012

(30) Foreign Application Priority Data
Aug. 10, 2009 (JP) .................................. 2009-185455

(51) Int. Cl.
*A61K 38/00* (2006.01)
*A61P 9/10* (2006.01)
*A61P 27/02* (2006.01)
*A61K 38/16* (2006.01)

(52) U.S. Cl.
USPC ........................................ 514/20.8; 514/21.2

(58) Field of Classification Search
None
See application file for complete search history.

(56) References Cited

FOREIGN PATENT DOCUMENTS

| JP | 2006-217866 A | 8/2006 |
|---|---|---|
| JP | 2008-162983 A | 7/2008 |
| JP | 2009-213430 A | 9/2009 |
| WO | WO 2007/131180 A2 | 11/2007 |
| WO | WO 2009/025819 A1 | 2/2009 |
| WO | WO 2009/119782 A1 | 10/2009 |
| WO | WO 2010/056970 A2 | 5/2010 |
| WO | WO 2011/005978 * | 1/2011 |

OTHER PUBLICATIONS

Bi et al., "Ectopic Expression of a Microbial-Type Rhodopsin Restores Visual Responses in Mice with Photoreceptor Degeneration", Neuron, vol. 50, No. 1, pp. 23-33, Apr. 6, 2006.
Han, et al., "Informational lesions: optical perturbation of spike timing and neural synchrony via microbial opsin gene fusions", Molecular Neuroscience, vol. 2, Article 12, pp. 1-9, Aug. 27, 2009.
International Search Report, dated Sep. 7, 2010, issued in PCT/JP2010/063786.
Kianianmomeni et al., "Channelrhodopsins of *Volvox carteri* Are Photochromic Proteins That Are Specifically Expressed in Somatic Cells under Control of Light, Temperature, and the Sex Inducer", Plant Physiology, vol. 151, No. 1, pp. 347-366, Sep. 2009.
Lin et al., "Characterization of Engineered Channelrhodopsin Variants with Improved Properties and Kinetics", Biophysical Journal, vol. 96, No. 5, pp. 1803-1814, Mar. 4, 2009.
Tomita et al., "Channelrhodopsin-2 gene transduced into retinal ganglion cells restores functional vision in genetically blind rats", Experimental Eye Research, vol. 90, No. 3, pp. 429-436, Mar. 2010.
Tomita et al., "Restoration of Visual Response in Aged Dystrophic RCS Rats Using AAV-Mediated Channelopsin-2 Gene Transfer", Investigative Ophthalology & Visual Science, vol. 48, No. 8, pp. 3821-3826, 2007.
Tsunoda et al., "Glu 87 of Channelrhodopsin-1 Causes pH-dependent Color Tuning and Fast Photocurrent Inactivation", Photochemistry and Photobiology, vol. 85, No. 2, pp. 564-569, 2009.
Wang et al., "Molecular Determinants Differentiating Photocurrent Properties of Two Channelrhodopsins from Chlamydomonas", The Journal of Biological Chemistry, vol. 284, No. 9, pp. 5685-5696, Feb. 27, 2009.
Zemelman et al., "Selective Photostimulation of Genetically ChARGed Neurons", Neuron, vol. 33, No. 1, pp. 15-22, Jan. 3, 2002.
Zhang et al., "Red-shifted optogenetic excitation: a tool for fast neural control derived from *Volvox carteri*", Nature Neuroscience, vol. 11, No. 6, pp. 631-633, 2008.
European Search Report dated Dec. 10, 2012 issued in connection with European Application No. 10808264.5.

* cited by examiner

*Primary Examiner* — Marcela M Cordero Garcia
*Assistant Examiner* — Sergio Coffa
(74) *Attorney, Agent, or Firm* — Birch, Stewart, Kolasch & Birch, LLP

(57) ABSTRACT

Disclosed is a Volvox carteri-derived light-receiving channel rhodopsin with an improved expression efficiency on a cell membrane. Specifically disclosed is a modified Volvox carteri-derived light-receiving channel rhodopsin protein. The protein is modified to contain an N-terminal region of *Chlamydomonas reinhardtii*-derived channel rhodopsin-1 at the N-terminal of the Volvox carteri-derived light-receiving channel rhodopsin protein, wherein the N-terminal region is involved in cell membrane-localized expression and contains no transmembrane domain of the *Chlamydomonas reinhardtii*-derived channel rhodopsin-1.

16 Claims, 6 Drawing Sheets
(2 of 6 Drawing Sheet(s) Filed in Color)

Fig. 2

ChR-HSB
Clamydomonas ChR1
Volvox ChR2

ATGTCGCGAGGCCATGGCTTCTTTGCCCTAGCGCTGGCAGTG
GCGCTGGCGGCGGGCAGTCAGGAGGCAGGAGCCTCGACTGGCAGTGA
CGCGAGGGTGCCGGTGCCGACGAGCGACTCAGGATGCCCGACTACGT
TTTCCACCGTGCCCACGAGCGGAATGCTCTTCCAAACCTCATAC
ACTCTTGAGAACAATGGTTCTGTTATTTGCATCGGAACAACGG
CGACGGTGTCTTCTGCATGAAATGGCTTAAGTCCAAGGGTTCA
CCTGTAGCGCTGAAGATGCCAACGCCTACACTGACGCAGTGCCCAACG
TTGCCTTTGTCGGTCAATCCTCATATGCGCGCTGGGAGGCGAG
CGGAGAACCACCTGCGCGCTGGGAGGAGGTTTACCTAGCGCGCTG
CGTCGAGTTGAACCAAGGTCGTGACTTGCGAACGCAAGCGAGTG
GAGGAGCCCCGATGCGTTCTACCTTGCGAACGGCAACGAGTG
CTGTGGCTGCGGTACGCGGAGTCGTTGCTGTCCTCCGATGTCGGCACC
ATTCTCATCGACTTGCAATTTGACTGGCCATGCTGTCCGAAGGACTA
CAACAAGCGGACCATGCGGTCTACTGCGGCCAAACACA
AAGTGATTTTCTTCCTCCCGGTTGCATGCATGCATGTCAGCGCAAACACA
TCTTCCACGCCCGCCAAGGTGTATATTGAGTCGTACCACACGG
TCCCAAGGTCTGTCGTCAGCTGGTCTGCTGGATGTTCCCGTACTGTTCCT
GGCTGTCTTCGTGCATGGGGATGTTCCCGTACTGTTCCT
GTTGGGGCCGAGGCTTCGACATCTGAGCGTCTACGGTC
AACAATCGGTCACACCATTATCGACGTTCTCCCAAGATTCACGACGC
GGGTCTGCTGGGCCACTTCCTCCGCCAAGTTCAGAAGATCAG
ACATTGCTGTATGGCGATATCCGCAAGGTTCAGAAGATCAG
GTCGCCGGTGAGGAGCTGGAGGTGGAGACCCTCATGACGGA
GGAGGCCCCC

Clamydomonas ChR1: AF385748
Volvox ChR2: EU285660 hChR-YR
Clamydomonas ChR1
Volvox ChR1

ATGTCGCGGAGGCCATGGCTTCTTTGCCCTAGCGCTGGCAGTG
GCGCTGGCGGCGGGCAGCCAGGAGCCTCGACTGGCAGTGA
CGGGACGGTGCCGGTGCCGACTCAGGATGCCCGACTACGT
TTTCCACCGTGCCCACGAGCGGAATGCTCTTCCAAACCTCATAC
ACTCTTGAGAACAATGGTTCTGTTATTTGCATCGGAACGGACA
GTGTTACTGTGAAGGTTGGCTTCGAGTCGGCGCAGTTCCATT
GAAAAGACAATAGGAATTACTCTTCAGTGGTAGTCTTTGCTT
GTCAGTGGCTTGCCTGGGGTGGTATCTCAAGCGTGGCG
AGCTACCTGCGGATGGGAGGAGGTTTACGTAGCCTTGATAGAA
ATGATGAAAAGCATCATCGAGGCCTTCACCCTGTCGACAGCC
CTGCAACACTGGTGTTGTGTTCTTCAGGAACGGCGTAGTTTGGAT
GCGGTATGCGGAACTCACAGGCCTGAAAGGACACATCGTGTG
GGACTATGGGCCGTTGGTTTCGATGTGGGATGCATCGATC
GGGCGCAACCAGCGCCATGTGACTATGGTGAGGAAGATCCT
GTTCTTCCTCATCTCATTGAGCTATGGTATGTATCGTATTTCA
TGGTGCTAAAGTTTATATCGAGAACTGGCCGAGTGATCATTCAAAAG
GGATTTGTCGAGAACTGGTCCGAGTCCGTTCTGCTGGCACG
TGTGGCTTGGGGAATGTTCCAGTCCTCTATGGATCGTGCCATTGGGC
GAAGGATTCGGTCATATCAGCTCGACCTCAAAGAACATGTGGGTGCT
ACTCCATTCTCGACCTGATTGCAAAGAAGCAGAAAATTAGCGCCGCC
GGGGAATTACCTGCGCGTCAAAAGAAGACACATCCGCCTGTG
TATGGCACATCAGAAGAAGCAGAAAATTAGGCGCCGCC
AAGAGATGGAGGTTGAGACACTGGTGCCTGAAGAGGAGACC
GG

Clamydomonas ChR1: AF385748
Volvox ChR1: EU622855

SEQUENCE LISTING

<160> NUMBER OF SEQ ID NOS: 10

<210> SEQ ID NO 1
<211> LENGTH: 2236
<212> TYPE: DNA
<213> ORGANISM: Chlamydomonas reinhardtii
<220> FEATURE:
<221> NAME/KEY: CDS
<222> LOCATION: (98)..(2236)

<400> SEQUENCE: 1

```
gcgttgcttg actacgcttc gctgtaataa tagcagcgcc acaagtagtg tcgccaaaca        60
actctcactt tgagcttgag cacaccgctg agccccg atg tcg cgg agg cca tgg       115
                                        Met Ser Arg Arg Pro Trp
                                         1               5 ctt ctt gcc cta gcg ctg gca gtg gcg ctg gcg gcc ggc agc gca gga        163
Leu Leu Ala Leu Ala Leu Ala Val Ala Leu Ala Ala Gly Ser Ala Gly
             10                  15                  20 gcc tcg act ggc agt gac gcg acg gtg ccg gtc gcg act cag gat ggc        211
Ala Ser Thr Gly Ser Asp Ala Thr Val Pro Val Ala Thr Gln Asp Gly
         25                  30                  35 ccc gac tac gtt ttc cac cgt gcc cac gag cgc atg ctc ttc caa acc        259
Pro Asp Tyr Val Phe His Arg Ala His Glu Arg Met Leu Phe Gln Thr
 40                  45                  50 tca tac act ctt gag aac aat ggt tct gtt att tgc atc ccg aac aac        307
Ser Tyr Thr Leu Glu Asn Asn Gly Ser Val Ile Cys Ile Pro Asn Asn
 55                  60                  65                  70 ggc cag tgc ttc tgc ttg gct tgg ctt aaa tcc aac gga aca aat gcc        355
Gly Gln Cys Phe Cys Leu Ala Trp Leu Lys Ser Asn Gly Thr Asn Ala
                 75                  80                  85 gag aag ttg gct gcc aac att ctg cag tgg att act ttt gcg ctt tca        403
Glu Lys Leu Ala Ala Asn Ile Leu Gln Trp Ile Thr Phe Ala Leu Ser
             90                  95                 100 gcg ctc tgc ctg atg ttc tac ggc tac cag acc tgg aag tct act tgc        451
Ala Leu Cys Leu Met Phe Tyr Gly Tyr Gln Thr Trp Lys Ser Thr Cys
        105                 110                 115 ggc tgg gag gag att tac gtg gcc acg atc gag atg atc aag ttc atc        499
Gly Trp Glu Glu Ile Tyr Val Ala Thr Ile Glu Met Ile Lys Phe Ile
    120                 125                 130 atc gag tat ttc cat gag ttt gac gaa cct gcg gtg atc tac tca tcc        547
Ile Glu Tyr Phe His Glu Phe Asp Glu Pro Ala Val Ile Tyr Ser Ser
135                 140                 145                 150 aac ggc aac aag acc gtg tgg ctt cgt tac gcg gag tgg ctg ctg acc        595
Asn Gly Asn Lys Thr Val Trp Leu Arg Tyr Ala Glu Trp Leu Leu Thr
                155                 160                 165 tgc cct gtc att ctt atc cat ctg agc aac ctt acg ggt ctg gcg aac        643
Cys Pro Val Ile Leu Ile His Leu Ser Asn Leu Thr Gly Leu Ala Asn
            170                 175                 180 gac tat aac aag cgt acc atg ggt ctg ctg gtg tca gat atc ggc acg        691
Asp Tyr Asn Lys Arg Thr Met Gly Leu Leu Val Ser Asp Ile Gly Thr
        185                 190                 195 atc gtg tgg ggc acc acg gcc gcg ctg tcc aag gga tac gtc cgt gtc        739
Ile Val Trp Gly Thr Thr Ala Ala Leu Ser Lys Gly Tyr Val Arg Val
    200                 205                 210 att ttc ttc ctg atg ggc ctg tgc tac ggc atc tac aca ttc ttc aac        787
Ile Phe Phe Leu Met Gly Leu Cys Tyr Gly Ile Tyr Thr Phe Phe Asn
215                 220                 225                 230 gca gcc aag gtc tac att gag gcg tac cac acc gtg ccc aag ggc att        835
Ala Ala Lys Val Tyr Ile Glu Ala Tyr His Thr Val Pro Lys Gly Ile
                235                 240                 245
```

-continued

| | | |
|---|---|---|
| tgc cgc gac ctg gtc cgc tac ctt gcc tgg ctc tac ttc tgt tca tgg<br>Cys Arg Asp Leu Val Arg Tyr Leu Ala Trp Leu Tyr Phe Cys Ser Trp<br>250                            255                        260 | 883 | |
| gct atg ttc ccg gtg ctg ttc ctg ctg ggc ccc gag ggc ttt ggc cac<br>Ala Met Phe Pro Val Leu Phe Leu Leu Gly Pro Glu Gly Phe Gly His<br>          265                        270                        275 | 931 | |
| atc aac caa ttc aac tct gcc atc gcc cac gcc atc ctg gac ctt gcc<br>Ile Asn Gln Phe Asn Ser Ala Ile Ala His Ala Ile Leu Asp Leu Ala<br>280                            285                        290 | 979 | |
| tcc aag aac gct tgg agt atg atg ggt cac ttt ctg cgt gtc aag atc<br>Ser Lys Asn Ala Trp Ser Met Met Gly His Phe Leu Arg Val Lys Ile<br>295                          300                        305                        310 | 1027 | |
| cac gag cac atc ctg ctg tac ggc gac atc cgc aag aag cag aag gtc<br>His Glu His Ile Leu Leu Tyr Gly Asp Ile Arg Lys Lys Gln Lys Val<br>               315                        320                        325 | 1075 | |
| aac gtg gct ggc cag gag atg gag gtg gag acc atg gtg cac gag gag<br>Asn Val Ala Gly Gln Glu Met Glu Val Glu Thr Met Val His Glu Glu<br>                    330                        335                        340 | 1123 | |
| gac gag gag acg cag aag gtg ccc acg gca aag tac gcc aac cgc gac<br>Asp Glu Glu Thr Gln Lys Val Pro Thr Ala Lys Tyr Ala Asn Arg Asp<br>345                            350                        355 | 1171 | |
| tcg ttc atc atc atg cgc gac cgc ctc aag gag aag ggc ttc gag acc<br>Ser Phe Ile Ile Met Arg Asp Arg Leu Lys Glu Lys Gly Phe Glu Thr<br>          360                        365                        370 | 1219 | |
| cgc gcc tcg ctg gac ggc gac ccg aac ggc gac gcc gag gcc aac gct<br>Arg Ala Ser Leu Asp Gly Asp Pro Asn Gly Asp Ala Glu Ala Asn Ala<br>375                            380                        385                        390 | 1267 | |
| gca gcc ggc ggc aag ccc gga atg gag atg ggc aag atg acc ggc atg<br>Ala Ala Gly Gly Lys Pro Gly Met Glu Met Gly Lys Met Thr Gly Met<br>                    395                        400                        405 | 1315 | |
| ggc atg ggc atg ggt gcc ggc atg ggc atg gcg acc atc gat tcg ggc<br>Gly Met Gly Met Gly Ala Gly Met Gly Met Ala Thr Ile Asp Ser Gly<br>               410                        415                        420 | 1363 | |
| cgc gtc atc ctc gcc gtg ccg gac atc tcc atg gtg gac ttt ttc cgc<br>Arg Val Ile Leu Ala Val Pro Asp Ile Ser Met Val Asp Phe Phe Arg<br>          425                        430                        435 | 1411 | |
| gag cag ttc gcg cgg ctg ccc gtg ccc tac gaa ctg gtg ccc gcg ctg<br>Glu Gln Phe Ala Arg Leu Pro Val Pro Tyr Glu Leu Val Pro Ala Leu<br>440                            445                        450 | 1459 | |
| ggc gcg gag aac acc ctc cag ctg gtg cag cag gcg cag tca ctg gga<br>Gly Ala Glu Asn Thr Leu Gln Leu Val Gln Gln Ala Gln Ser Leu Gly<br>455                            460                        465                        470 | 1507 | |
| ggc tgc gac ttc gtc ctc atg cac ccc gag ttc ctg cgc gac cgc agt<br>Gly Cys Asp Phe Val Leu Met His Pro Glu Phe Leu Arg Asp Arg Ser<br>                    475                        480                        485 | 1555 | |
| ccc acg ggt ctg ctg ccc cgc ctc aag atg ggg cag cgc gcc gcg<br>Pro Thr Gly Leu Leu Pro Arg Leu Lys Met Gly Gln Arg Ala Ala<br>                        490                        495                        500 | 1603 | |
| gcc ttc ggc tgg gcg gca atc ggc ccc atg cgg gac ttg atc gag ggt<br>Ala Phe Gly Trp Ala Ala Ile Gly Pro Met Arg Asp Leu Ile Glu Gly<br>               505                        510                        515 | 1651 | |
| tcg ggc gtt gac ggc tgg ctg gag ggc ccc agc ttt ggc gcc ggc atc<br>Ser Gly Val Asp Gly Trp Leu Glu Gly Pro Ser Phe Gly Ala Gly Ile<br>          520                        525                        530 | 1699 | |
| aac cag cag gcg ctg gtg gcg ctg atc aac cgc atg cag cag gcc aag<br>Asn Gln Gln Ala Leu Val Ala Leu Ile Asn Arg Met Gln Gln Ala Lys<br>535                            540                        545                        550 | 1747 | |
| aag atg ggc atg atg ggc ggt atg ggt atg ggc atg ggc ggc ggc atg<br>Lys Met Gly Met Met Gly Gly Met Gly Met Gly Met Gly Gly Gly Met<br>                    555                        560                        565 | 1795 | |

-continued

| | | |
|---|---|---|
| ggt atg ggc atg ggt atg ggc atg ggc atg gcc ccc agc atg aac gcc<br>Gly Met Gly Met Gly Met Gly Met Gly Met Ala Pro Ser Met Asn Ala<br>570              575                 580 | 1843 | |
| ggc atg act ggc ggc atg ggc ggc gcc tcc atg ggc ggt gcc gtg atg<br>Gly Met Thr Gly Gly Met Gly Gly Ala Ser Met Gly Gly Ala Val Met<br>585              590               595 | 1891 | |
| ggc atg ggc atg ggc atg cag ccc atg cag cag gct atg ccg gcc atg<br>Gly Met Gly Met Gly Met Gln Pro Met Gln Gln Ala Met Pro Ala Met<br>600              605               610 | 1939 | |
| tcg ccc atg atg act cag cag ccc agc atg atg agt cag ccc tcc gcc<br>Ser Pro Met Met Thr Gln Gln Pro Ser Met Met Ser Gln Pro Ser Ala<br>615              620               625               630 | 1987 | |
| atg agc gcc ggc ggc gcc atg cag gcc atg ggt ggc gtc atg ccc agc<br>Met Ser Ala Gly Gly Ala Met Gln Ala Met Gly Gly Val Met Pro Ser<br>635              640               645 | 2035 | |
| ccc gcc ccc ggc ggc cgc gtg ggc acc aac ccg ctg ttt ggc tct gcg<br>Pro Ala Pro Gly Gly Arg Val Gly Thr Asn Pro Leu Phe Gly Ser Ala<br>650              655               660 | 2083 | |
| ccc tct ccg ctg agc tcg cag ccc ggc atc agc cct ggc atg gcg acg<br>Pro Ser Pro Leu Ser Ser Gln Pro Gly Ile Ser Pro Gly Met Ala Thr<br>665            670               675 | 2131 | |
| ccg ccc gcc gcc acc gcc gca ccc gcc gct ggc ggc agc gag gcc gag<br>Pro Pro Ala Ala Thr Ala Ala Pro Ala Ala Gly Gly Ser Glu Ala Glu<br>680              685               690 | 2179 | |
| atg ctg cag cag ctg atg agc gag atc aac cgc ctg aag aac gag ctg<br>Met Leu Gln Gln Leu Met Ser Glu Ile Asn Arg Leu Lys Asn Glu Leu<br>695            700               705               710 | 2227 | |
| ggc gag taa<br>Gly Glu | 2236 | |

<210> SEQ ID NO 2
<211> LENGTH: 712
<212> TYPE: PRT
<213> ORGANISM: Chlamydomonas reinhardtii

<400> SEQUENCE: 2

Met Ser Arg Arg Pro Trp Leu Leu Ala Leu Ala Leu Ala Val Ala Leu
1                     5                    10                  15

Ala Ala Gly Ser Ala Gly Ala Ser Thr Gly Ser Asp Ala Thr Val Pro
               20                    25                    30

Val Ala Thr Gln Asp Gly Pro Asp Tyr Val Phe His Arg Ala His Glu
               35                    40                    45

Arg Met Leu Phe Gln Thr Ser Tyr Thr Leu Glu Asn Asn Gly Ser Val
    50                    55                    60

Ile Cys Ile Pro Asn Asn Gly Gln Cys Phe Cys Leu Ala Trp Leu Lys
65                    70                    75                    80

Ser Asn Gly Thr Asn Ala Glu Lys Leu Ala Ala Asn Ile Leu Gln Trp
               85                    90                    95

Ile Thr Phe Ala Leu Ser Ala Leu Cys Leu Met Phe Tyr Gly Tyr Gln
              100                   105                 110

Thr Trp Lys Ser Thr Cys Gly Trp Glu Glu Ile Tyr Val Ala Thr Ile
             115                   120                 125

Glu Met Ile Lys Phe Ile Ile Glu Tyr Phe His Glu Phe Asp Glu Pro
130                  135                   140

Ala Val Ile Tyr Ser Ser Asn Gly Asn Lys Thr Val Trp Leu Arg Tyr
145                  150                   155                  160

Ala Glu Trp Leu Leu Thr Cys Pro Val Ile Leu Ile His Leu Ser Asn
              165                   170                 175

-continued

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
    290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Glu Thr Gln Lys Val Pro Thr Ala
            340                 345                 350

Lys Tyr Ala Asn Arg Asp Ser Phe Ile Ile Met Arg Asp Arg Leu Lys
    355                 360                 365

Glu Lys Gly Phe Glu Thr Arg Ala Ser Leu Asp Gly Asp Pro Asn Gly
370                 375                 380

Asp Ala Glu Ala Asn Ala Ala Gly Gly Lys Pro Gly Met Glu Met
385                 390                 395                 400

Gly Lys Met Thr Gly Met Gly Met Gly Met Ala Gly Met Gly Met
                405                 410                 415

Ala Thr Ile Asp Ser Gly Arg Val Ile Leu Ala Val Pro Asp Ile Ser
            420                 425                 430

Met Val Asp Phe Phe Arg Glu Gln Phe Ala Arg Leu Pro Val Pro Tyr
        435                 440                 445

Glu Leu Val Pro Ala Leu Gly Ala Glu Asn Thr Leu Gln Leu Val Gln
    450                 455                 460

Gln Ala Gln Ser Leu Gly Gly Cys Asp Phe Val Leu Met His Pro Glu
465                 470                 475                 480

Phe Leu Arg Asp Arg Ser Pro Thr Gly Leu Leu Pro Arg Leu Lys Met
                485                 490                 495

Gly Gly Gln Arg Ala Ala Ala Phe Gly Trp Ala Ala Ile Gly Pro Met
            500                 505                 510

Arg Asp Leu Ile Glu Gly Ser Gly Val Asp Gly Trp Leu Glu Gly Pro
        515                 520                 525

Ser Phe Gly Ala Gly Ile Asn Gln Gln Ala Leu Val Ala Leu Ile Asn
    530                 535                 540

Arg Met Gln Gln Ala Lys Lys Met Gly Met Met Gly Met Gly Met
545                 550                 555                 560

Gly Met Gly Gly Gly Met Gly Met Gly Met Gly Met Gly Met
                565                 570                 575

Ala Pro Ser Met Asn Ala Gly Met Thr Gly Met Gly Gly Ala Ser
            580                 585                 590

Met Gly Gly Ala Val Met Gly Met Gly Met Gly Met Gln Pro Met Gln

-continued

```
                595                 600                 605
Gln Ala Met Pro Ala Met Ser Pro Met Met Thr Gln Gln Pro Ser Met
    610                 615                 620
Met Ser Gln Pro Ser Ala Met Ser Ala Gly Gly Ala Met Gln Ala Met
625                 630                 635                 640
Gly Gly Val Met Pro Ser Pro Ala Pro Gly Gly Arg Val Gly Thr Asn
                645                 650                 655
Pro Leu Phe Gly Ser Ala Pro Ser Pro Leu Ser Ser Gln Pro Gly Ile
            660                 665                 670
Ser Pro Gly Met Ala Thr Pro Pro Ala Ala Thr Ala Ala Pro Ala Ala
        675                 680                 685
Gly Gly Ser Glu Ala Glu Met Leu Gln Gln Leu Met Ser Glu Ile Asn
    690                 695                 700
Arg Leu Lys Asn Glu Leu Gly Glu
705                 710

<210> SEQ ID NO 3
<211> LENGTH: 903
<212> TYPE: DNA
<213> ORGANISM: Artificial
<220> FEATURE:
<223> OTHER INFORMATION: Synthetic construct channel rhodopsin 1 (ChR1)
      gene derived from Volvox carteri
<220> FEATURE:
<221> NAME/KEY: CDS
<222> LOCATION: (1)..(903)

<400> SEQUENCE: 3 atg gac tat cct gtt gct aga agc ctc ata gtt cgc tac cca acc gac      48
Met Asp Tyr Pro Val Ala Arg Ser Leu Ile Val Arg Tyr Pro Thr Asp
1               5                   10                  15 ctc gga aac ggc acc gtc tgc atg cca aga gga cag tgt tac tgt gaa      96
Leu Gly Asn Gly Thr Val Cys Met Pro Arg Gly Gln Cys Tyr Cys Glu
            20                  25                  30 ggt tgg ctt cgg agt cgc ggc act tcc att gaa aag aca ata gca att     144
Gly Trp Leu Arg Ser Arg Gly Thr Ser Ile Glu Lys Thr Ile Ala Ile
        35                  40                  45 act ctt cag tgg gta gtc ttt gct ttg tca gtg gct tgc ctg ggg tgg     192
Thr Leu Gln Trp Val Val Phe Ala Leu Ser Val Ala Cys Leu Gly Trp
    50                  55                  60 tat gcg tat caa gcg tgg cga gct acc tgc gga tgg gag gag gtt tac     240
Tyr Ala Tyr Gln Ala Trp Arg Ala Thr Cys Gly Trp Glu Glu Val Tyr
65                  70                  75                  80 gta gcc ttg ata gaa atg atg aaa agc atc atc gag gcc ttc cac gag     288
Val Ala Leu Ile Glu Met Met Lys Ser Ile Ile Glu Ala Phe His Glu
                85                  90                  95 ttc gac agc cct gca aca ctg tgg ctg tct tca ggg aac ggc gta gtt     336
Phe Asp Ser Pro Ala Thr Leu Trp Leu Ser Ser Gly Asn Gly Val Val
            100                 105                 110 tgg atg cgg tat ggc gaa tgg ctc ctc acc tgc ccg gtc ctt ctg atc     384
Trp Met Arg Tyr Gly Glu Trp Leu Leu Thr Cys Pro Val Leu Leu Ile
        115                 120                 125 cat ctg agc aac ctc aca ggc ctg aag gac gat tat agc aaa agg act     432
His Leu Ser Asn Leu Thr Gly Leu Lys Asp Asp Tyr Ser Lys Arg Thr
    130                 135                 140 atg ggc ctg ttg gtt tct gat gtg gga tgc atc gtg tgg ggc gca acc     480
Met Gly Leu Leu Val Ser Asp Val Gly Cys Ile Val Trp Gly Ala Thr
145                 150                 155                 160 agc gcc atg tgt acg ggg tgg acg aag atc ctg ttc ttc ctc atc tca     528
Ser Ala Met Cys Thr Gly Trp Thr Lys Ile Leu Phe Phe Leu Ile Ser
                165                 170                 175
```

| | | | | | | | | | | | | | | | | |
|---|---|---|---|---|---|---|---|---|---|---|---|---|---|---|---|---|
| ttg | agc | tat | ggt | atg | tat | acc | tat | ttt | cat | gct | gct | aaa | gtt | tat | atc | 576 |
| Leu | Ser | Tyr | Gly | Met | Tyr | Thr | Tyr | Phe | His | Ala | Ala | Lys | Val | Tyr | Ile | |
| | | | 180 | | | | | 185 | | | | | 190 | | | |
| gaa | gca | ttc | cac | aca | gtt | cca | aaa | ggg | att | tgt | cga | gaa | ctg | gtc | cga | 624 |
| Glu | Ala | Phe | His | Thr | Val | Pro | Lys | Gly | Ile | Cys | Arg | Glu | Leu | Val | Arg | |
| | | | | 195 | | | | | 200 | | | | | 205 | | |
| gtg | atg | gcc | tgg | aca | ttc | ttt | gtg | gct | tgg | gga | atg | ttt | cca | gtc | ctg | 672 |
| Val | Met | Ala | Trp | Thr | Phe | Phe | Val | Ala | Trp | Gly | Met | Phe | Pro | Val | Leu | |
| 210 | | | | | 215 | | | | | 220 | | | | | | |
| ttt | ctg | ctg | ggc | acg | gaa | gga | ttc | ggt | cat | atc | agc | cct | tat | gga | tct | 720 |
| Phe | Leu | Leu | Gly | Thr | Glu | Gly | Phe | Gly | His | Ile | Ser | Pro | Tyr | Gly | Ser | |
| 225 | | | | | 230 | | | | | 235 | | | | | 240 | |
| gcc | att | ggg | cac | tcc | atc | ctc | gac | ctg | att | gca | aag | aac | atg | tgg | ggt | 768 |
| Ala | Ile | Gly | His | Ser | Ile | Leu | Asp | Leu | Ile | Ala | Lys | Asn | Met | Trp | Gly | |
| | | | | 245 | | | | | 250 | | | | | 255 | | |
| gtg | ctg | ggg | aat | tac | ctg | cgc | gtc | aaa | atc | cac | gag | cac | atc | ctg | ttg | 816 |
| Val | Leu | Gly | Asn | Tyr | Leu | Arg | Val | Lys | Ile | His | Glu | His | Ile | Leu | Leu | |
| | | | 260 | | | | | 265 | | | | | 270 | | | |
| tat | ggc | gac | atc | aga | aag | aag | cag | aaa | att | acg | atc | gcc | ggc | caa | gag | 864 |
| Tyr | Gly | Asp | Ile | Arg | Lys | Lys | Gln | Lys | Ile | Thr | Ile | Ala | Gly | Gln | Glu | |
| | | | | 275 | | | | | 280 | | | | | 285 | | |
| atg | gag | gtt | gag | aca | ctg | gtg | gct | gaa | gag | gag | gac | taa | | | | 903 |
| Met | Glu | Val | Glu | Thr | Leu | Val | Ala | Glu | Glu | Glu | Asp | | | | | |
| | | | 290 | | | | | 295 | | | | 300 | | | | |

<210> SEQ ID NO 4
<211> LENGTH: 300
<212> TYPE: PRT
<213> ORGANISM: Artificial
<220> FEATURE:
<223> OTHER INFORMATION: Synthetic construct channel rhodopsin 1 (ChR1)
      gene derived from Volvox carteri

<400> SEQUENCE: 4

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

-continued

```
Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 5
<211> LENGTH: 2411
<212> TYPE: DNA
<213> ORGANISM: Volvox carteri f. nagariensis
<220> FEATURE:
<221> NAME/KEY: CDS
<222> LOCATION: (46)..(2289)

<400> SEQUENCE: 5
agaaaaacgc tttaagcaag aagaaaacgg ttcaccagca caaga atg gac cac cca      57
                                                Met Asp His Pro
                                                  1 gtt gcg cgg tcc ctc atc ggc tca agt tat act aac ctc aat aat ggc      105
Val Ala Arg Ser Leu Ile Gly Ser Ser Tyr Thr Asn Leu Asn Asn Gly
  5                  10                  15                  20 tcc att gtg att cca tct gac gcg tgc ttc tgc atg aaa tgg ctt aag      153
Ser Ile Val Ile Pro Ser Asp Ala Cys Phe Cys Met Lys Trp Leu Lys
                 25                  30                  35 tcc aag ggt tca cct gta gcg ctg aag atg gcc aac gcg cta cag tgg      201
Ser Lys Gly Ser Pro Val Ala Leu Lys Met Ala Asn Ala Leu Gln Trp
             40                  45                  50 gcg gcc ttc gct ttg tcg gtc ata atc ctc atc tac tat gca tac gcg      249
Ala Ala Phe Ala Leu Ser Val Ile Ile Leu Ile Tyr Tyr Ala Tyr Ala
         55                  60                  65 acc tgg aga acc acc tgc ggc tgg gag gag gta tat gtg tgc tgc gtc      297
Thr Trp Arg Thr Thr Cys Gly Trp Glu Glu Val Tyr Val Cys Cys Val
     70                  75                  80 gag ttg acc aag gtc gtg atc gag ttc ttc cac gag ttt gac gag ccc      345
Glu Leu Thr Lys Val Val Ile Glu Phe Phe His Glu Phe Asp Glu Pro
 85                  90                  95                 100 ggc atg ctg tac ctt gcg aac ggc aac cga gtg ctg tgg ctg cgg tac      393
Gly Met Leu Tyr Leu Ala Asn Gly Asn Arg Val Leu Trp Leu Arg Tyr
                105                 110                 115 ggc gag tgg ttg ctg acc tgc ccc gtc att ctc atc cac ttg tcc aat      441
Gly Glu Trp Leu Leu Thr Cys Pro Val Ile Leu Ile His Leu Ser Asn
            120                 125                 130 ttg act ggc ctc aag gac gac tac aac aag cgg acc atg cgg ttg ctt      489
Leu Thr Gly Leu Lys Asp Asp Tyr Asn Lys Arg Thr Met Arg Leu Leu
        135                 140                 145 gtc tcc gat gtc ggc acc atc gtg tgg ggt gct act gcg gcc atg tcc      537
Val Ser Asp Val Gly Thr Ile Val Trp Gly Ala Thr Ala Ala Met Ser
    150                 155                 160 act ggc tac ata aaa gtg att ttc ttc ctc ctc ggt tgc atg tac ggc      585
Thr Gly Tyr Ile Lys Val Ile Phe Phe Leu Leu Gly Cys Met Tyr Gly
165                 170                 175                 180
```

```
gca aac aca ttc ttc cac gcc gcc aag gtg tat att gag tcg tac cac      633
Ala Asn Thr Phe Phe His Ala Ala Lys Val Tyr Ile Glu Ser Tyr His
            185                 190                 195 acc gtc ccc aag ggt ctg tgt cgt cag ctg gtc cgc gcc atg gcc tgg      681
Thr Val Pro Lys Gly Leu Cys Arg Gln Leu Val Arg Ala Met Ala Trp
            200                 205                 210 ctg ttc ttc gtg tca tgg ggg atg ttt ccc gta ctg ttc ctg ttg ggg      729
Leu Phe Phe Val Ser Trp Gly Met Phe Pro Val Leu Phe Leu Leu Gly
            215                 220                 225 ccc gag ggc ttc gga cat ctg agc gtc tac ggg tca aca atc ggt cac      777
Pro Glu Gly Phe Gly His Leu Ser Val Tyr Gly Ser Thr Ile Gly His
            230                 235                 240 acc att atc gac ctt ctc tcc aag aac tgc tgg ggt ctg ctg ggc cac      825
Thr Ile Ile Asp Leu Leu Ser Lys Asn Cys Trp Gly Leu Leu Gly His
245                 250                 255                 260 ttc ctc cgc ctg aag att cac gag cac att ctg ctg tat ggc gat atc      873
Phe Leu Arg Leu Lys Ile His Glu His Ile Leu Leu Tyr Gly Asp Ile
            265                 270                 275 cgc aag gtt cag aag atc agg gtg gcc ggt gag gag ctg gag gtg gag      921
Arg Lys Val Gln Lys Ile Arg Val Ala Gly Glu Glu Leu Glu Val Glu
            280                 285                 290 acc ctc atg acg gag gag gcc ccc gac acc gtc aag aag tcc act gcg      969
Thr Leu Met Thr Glu Glu Ala Pro Asp Thr Val Lys Lys Ser Thr Ala
            295                 300                 305 cag tac gcc aac agg gag tcc ttc ttg acc atg cgt gat aag ctc aag     1017
Gln Tyr Ala Asn Arg Glu Ser Phe Leu Thr Met Arg Asp Lys Leu Lys
            310                 315                 320 gag aag ggt ttc gaa gtg cgt gct tcg ctg gat aac agc ggc ata gac     1065
Glu Lys Gly Phe Glu Val Arg Ala Ser Leu Asp Asn Ser Gly Ile Asp
325                 330                 335                 340 gcc gtt atc aac cac aac aac aac tac aat aac gcc cta gca aac gcc     1113
Ala Val Ile Asn His Asn Asn Asn Tyr Asn Asn Ala Leu Ala Asn Ala
            345                 350                 355 gca gca gca gtc ggc aag ccg ggc atg gag ctc tct aag ctc gac cac     1161
Ala Ala Ala Val Gly Lys Pro Gly Met Glu Leu Ser Lys Leu Asp His
            360                 365                 370 gtc gcc gcc aac gcc gcc ggc atg ggc ggc atc gcg gac cat gtt gcc     1209
Val Ala Ala Asn Ala Ala Gly Met Gly Gly Ile Ala Asp His Val Ala
            375                 380                 385 acc acc tcg ggc gcc atc tcc ccc ggc cgc gtc atc cta gcc gta cct     1257
Thr Thr Ser Gly Ala Ile Ser Pro Gly Arg Val Ile Leu Ala Val Pro
            390                 395                 400 gat att tcc atg gtg gac tat ttc agg gag cag ttt gcg cag ctg ccg     1305
Asp Ile Ser Met Val Asp Tyr Phe Arg Glu Gln Phe Ala Gln Leu Pro
405                 410                 415                 420 gtg cag tac gaa gtc gta ccc gcg ctc ggc gcc gac aat gcc gta cag     1353
Val Gln Tyr Glu Val Val Pro Ala Leu Gly Ala Asp Asn Ala Val Gln
            425                 430                 435 ctt gtt gta cag gct gct ggg ctg ggc ggc tgc gac ttt gta ctc cta     1401
Leu Val Val Gln Ala Ala Gly Leu Gly Gly Cys Asp Phe Val Leu Leu
            440                 445                 450 cat ccg gag ttt ctc cgt gac aag tct tcc acc agc ttg cct gct cgg     1449
His Pro Glu Phe Leu Arg Asp Lys Ser Ser Thr Ser Leu Pro Ala Arg
            455                 460                 465 ctg cgg tcc ata ggg cag cgt gtg gca gca ttc ggc tgg tcc ccc gtt     1497
Leu Arg Ser Ile Gly Gln Arg Val Ala Ala Phe Gly Trp Ser Pro Val
            470                 475                 480 ggc cct gtg cgt gat ctc att gaa tcc gct ggc ctg gat ggc tgg ctg     1545
Gly Pro Val Arg Asp Leu Ile Glu Ser Ala Gly Leu Asp Gly Trp Leu
485                 490                 495                 500
```

```
gag ggg ccc agt ttt gga ttg ggc att agc ctg ccc aac ctt gca agc    1593
Glu Gly Pro Ser Phe Gly Leu Gly Ile Ser Leu Pro Asn Leu Ala Ser
            505                 510                 515 ctg gtc ctg cgg atg cag cat gcg cgc aag atg gcg gcg atg ttg ggc    1641
Leu Val Leu Arg Met Gln His Ala Arg Lys Met Ala Ala Met Leu Gly
        520                 525                 530 ggc atg ggt ggc atg ctc ggc agc aac ttg atg tct ggc agt ggt ggc    1689
Gly Met Gly Gly Met Leu Gly Ser Asn Leu Met Ser Gly Ser Gly Gly
    535                 540                 545 gtt ggg ctg atg ggc gcg ggc tcc ccg gga ggc ggc ggc gcg atg        1737
Val Gly Leu Met Gly Ala Gly Ser Pro Gly Gly Gly Gly Ala Met
550                 555                 560 ggc gtg ggg atg acg ggc atg ggc atg gtg ggc act aat gcc atg ggg    1785
Gly Val Gly Met Thr Gly Met Gly Met Val Gly Thr Asn Ala Met Gly
565                 570                 575                 580 cgc ggc gct gtc ggc aac agt gtg gcg aat gcc tcg atg gga ggt ggt    1833
Arg Gly Ala Val Gly Asn Ser Val Ala Asn Ala Ser Met Gly Gly Gly
            585                 590                 595 tcg gcc ggc atg ggc atg ggg atg atg ggc atg gtg ggc gct ggc gtt    1881
Ser Ala Gly Met Gly Met Gly Met Met Gly Met Val Gly Ala Gly Val
        600                 605                 610 gga gga cag cag caa atg ggc gcg aac ggc atg ggc cct acg tct ttc    1929
Gly Gly Gln Gln Gln Met Gly Ala Asn Gly Met Gly Pro Thr Ser Phe
    615                 620                 625 cag ttg ggc agc aac ccg ctg tac aac acc gcg cca tcg ccg ctg agc    1977
Gln Leu Gly Ser Asn Pro Leu Tyr Asn Thr Ala Pro Ser Pro Leu Ser
630                 635                 640 tcc cag ccc gga ggc gac gct tcc gcc gcc gcc gcc gct gcc gcc gcc    2025
Ser Gln Pro Gly Gly Asp Ala Ser Ala Ala Ala Ala Ala Ala Ala Ala
645                 650                 655                 660 gcg gcg gct acc gga gca gcc agc aac agc atg aac gcc atg cag gcc    2073
Ala Ala Ala Thr Gly Ala Ala Ser Asn Ser Met Asn Ala Met Gln Ala
                665                 670                 675 ggc ggc tcc gtg cgc aac tct ggc atc ctg gcg ggc ggt ttg gga agc    2121
Gly Gly Ser Val Arg Asn Ser Gly Ile Leu Ala Gly Gly Leu Gly Ser
            680                 685                 690 atg atg ggg ccc ccg ggg gcg cct gct gcg ccg aca gcg gca gcg acg    2169
Met Met Gly Pro Pro Gly Ala Pro Ala Ala Pro Thr Ala Ala Ala Thr
        695                 700                 705 gcg gcg ccc gcc gtg acc atg ggg gca cct ggc ggc ggc ggc gcc gcc    2217
Ala Ala Pro Ala Val Thr Met Gly Ala Pro Gly Gly Gly Gly Ala Ala
    710                 715                 720 gct tct gag gct gag atg ctt cag caa ctg atg gcg gag att aac cgc    2265
Ala Ser Glu Ala Glu Met Leu Gln Gln Leu Met Ala Glu Ile Asn Arg
725                 730                 735                 740 ttg aag agc gag ttg ggc gag tga gctcgcggcc gggtgagagt ggagtggaat   2319
Leu Lys Ser Glu Leu Gly Glu
                745 ggagtggaat ggagtggaat ggagtggaat ggagtggaat ggagtggaat ggagtggaat  2379 ggagtggtac acgcttggtg ggacatccgg tc                                2411

<210> SEQ ID NO 6
<211> LENGTH: 747
<212> TYPE: PRT
<213> ORGANISM: Volvox carteri f. nagariensis

<400> SEQUENCE: 6

Met Asp His Pro Val Ala Arg Ser Leu Ile Gly Ser Ser Tyr Thr Asn
1               5                   10                  15

Leu Asn Asn Gly Ser Ile Val Ile Pro Ser Asp Ala Cys Phe Cys Met
```

-continued

```
            20                  25                  30
Lys Trp Leu Lys Ser Lys Gly Ser Pro Val Ala Leu Lys Met Ala Asn
             35                  40                  45

Ala Leu Gln Trp Ala Ala Phe Ala Leu Ser Val Ile Ile Leu Ile Tyr
 50                  55                  60

Tyr Ala Tyr Ala Thr Trp Arg Thr Thr Cys Gly Trp Glu Glu Val Tyr
 65                  70                  75                  80

Val Cys Cys Val Glu Leu Thr Lys Val Val Ile Glu Phe Phe His Glu
                 85                  90                  95

Phe Asp Glu Pro Gly Met Leu Tyr Leu Ala Asn Gly Asn Arg Val Leu
            100                 105                 110

Trp Leu Arg Tyr Gly Glu Trp Leu Leu Thr Cys Pro Val Ile Leu Ile
            115                 120                 125

His Leu Ser Asn Leu Thr Gly Leu Lys Asp Asp Tyr Asn Lys Arg Thr
            130                 135                 140

Met Arg Leu Leu Val Ser Asp Val Gly Thr Ile Val Trp Gly Ala Thr
145                 150                 155                 160

Ala Ala Met Ser Thr Gly Tyr Ile Lys Val Ile Phe Phe Leu Leu Gly
                165                 170                 175

Cys Met Tyr Gly Ala Asn Thr Phe Phe His Ala Ala Lys Val Tyr Ile
            180                 185                 190

Glu Ser Tyr His Thr Val Pro Lys Gly Leu Cys Arg Gln Leu Val Arg
            195                 200                 205

Ala Met Ala Trp Leu Phe Phe Val Ser Trp Gly Met Phe Pro Val Leu
            210                 215                 220

Phe Leu Leu Gly Pro Glu Gly Phe Gly His Leu Ser Val Tyr Gly Ser
225                 230                 235                 240

Thr Ile Gly His Thr Ile Ile Asp Leu Leu Ser Lys Asn Cys Trp Gly
                245                 250                 255

Leu Leu Gly His Phe Leu Arg Leu Lys Ile His Glu His Ile Leu Leu
            260                 265                 270

Tyr Gly Asp Ile Arg Lys Val Gln Lys Ile Arg Val Ala Gly Glu Glu
            275                 280                 285

Leu Glu Val Glu Thr Leu Met Thr Glu Glu Ala Pro Asp Thr Val Lys
            290                 295                 300

Lys Ser Thr Ala Gln Tyr Ala Asn Arg Glu Ser Phe Leu Thr Met Arg
305                 310                 315                 320

Asp Lys Leu Lys Glu Lys Gly Phe Glu Val Arg Ala Ser Leu Asp Asn
                325                 330                 335

Ser Gly Ile Asp Ala Val Ile Asn His Asn Asn Tyr Asn Asn Ala
            340                 345                 350

Leu Ala Asn Ala Ala Ala Ala Val Gly Lys Pro Gly Met Glu Leu Ser
            355                 360                 365

Lys Leu Asp His Val Ala Ala Asn Ala Ala Gly Met Gly Gly Ile Ala
            370                 375                 380

Asp His Val Ala Thr Thr Ser Gly Ala Ile Ser Pro Gly Arg Val Ile
385                 390                 395                 400

Leu Ala Val Pro Asp Ile Ser Met Val Asp Tyr Phe Arg Glu Gln Phe
                405                 410                 415

Ala Gln Leu Pro Val Gln Tyr Glu Val Val Pro Ala Leu Gly Ala Asp
            420                 425                 430

Asn Ala Val Gln Leu Val Val Gln Ala Ala Gly Leu Gly Gly Cys Asp
            435                 440                 445
```

```
Phe Val Leu Leu His Pro Glu Phe Leu Arg Asp Lys Ser Thr Ser
    450                 455                 460

Leu Pro Ala Arg Leu Arg Ser Ile Gly Gln Arg Val Ala Ala Phe Gly
465                 470                 475                 480

Trp Ser Pro Val Gly Pro Val Arg Asp Leu Ile Glu Ser Ala Gly Leu
                    485                 490                 495

Asp Gly Trp Leu Glu Gly Pro Ser Phe Gly Leu Gly Ile Ser Leu Pro
            500                 505                 510

Asn Leu Ala Ser Leu Val Leu Arg Met Gln His Ala Arg Lys Met Ala
        515                 520                 525

Ala Met Leu Gly Gly Met Gly Gly Met Leu Gly Ser Asn Leu Met Ser
    530                 535                 540

Gly Ser Gly Gly Val Gly Leu Met Gly Ala Gly Ser Pro Gly Gly Gly
545                 550                 555                 560

Gly Gly Ala Met Gly Val Gly Met Thr Gly Met Gly Met Val Gly Thr
                    565                 570                 575

Asn Ala Met Gly Arg Gly Ala Val Gly Asn Ser Val Ala Asn Ala Ser
            580                 585                 590

Met Gly Gly Gly Ser Ala Gly Met Gly Met Gly Met Gly Met Val
        595                 600                 605

Gly Ala Gly Val Gly Gly Gln Gln Gln Met Gly Ala Asn Gly Met Gly
610                 615                 620

Pro Thr Ser Phe Gln Leu Gly Ser Asn Pro Leu Tyr Asn Thr Ala Pro
625                 630                 635                 640

Ser Pro Leu Ser Ser Gln Pro Gly Gly Asp Ala Ser Ala Ala Ala
                    645                 650                 655

Ala Ala Ala Ala Ala Ala Ala Thr Gly Ala Ala Ser Asn Ser Met Asn
            660                 665                 670

Ala Met Gln Ala Gly Gly Ser Val Arg Asn Ser Gly Ile Leu Ala Gly
        675                 680                 685

Gly Leu Gly Ser Met Met Gly Pro Pro Gly Ala Pro Ala Ala Pro Thr
    690                 695                 700

Ala Ala Ala Thr Ala Ala Pro Ala Val Thr Met Gly Ala Pro Gly Gly
705                 710                 715                 720

Gly Gly Ala Ala Ala Ser Glu Ala Glu Met Leu Gln Gln Leu Met Ala
                    725                 730                 735

Glu Ile Asn Arg Leu Lys Ser Glu Leu Gly Glu
            740                 745

<210> SEQ ID NO 7
<211> LENGTH: 1035
<212> TYPE: DNA
<213> ORGANISM: Artificial
<220> FEATURE:
<223> OTHER INFORMATION: DNA encoding a fusion protein having
      transmembrane domains of volvox channel rhodopsin-2 and the
      N-terminus region of chamydomonas channel rhodopsin-1
<220> FEATURE:
<221> NAME/KEY: CDS
<222> LOCATION: (1)..(1035)

<400> SEQUENCE: 7 atg tcg cgg agg cca tgg ctt ctt gcc cta gcg ctg gca gtg gcg ctg      48
Met Ser Arg Arg Pro Trp Leu Leu Ala Leu Ala Leu Ala Val Ala Leu
1               5                   10                  15 gcg gcc ggc agc gca gga gcc tcg act ggc agt gac gcg acg gtg ccg      96
Ala Ala Gly Ser Ala Gly Ala Ser Thr Gly Ser Asp Ala Thr Val Pro
            20                  25                  30
```

```
gtc gcg act cag gat ggc ccc gac tac gtt ttc cac cgt gcc cac gag        144
Val Ala Thr Gln Asp Gly Pro Asp Tyr Val Phe His Arg Ala His Glu
         35                  40                  45 cgc atg ctc ttc caa acc tca tac act ctt gag aac aat ggt tct gtt        192
Arg Met Leu Phe Gln Thr Ser Tyr Thr Leu Glu Asn Asn Gly Ser Val
 50                  55                  60 att tgc atc ccg aac aac ggc gac gcg tgc ttc tgc atg aaa tgg ctt        240
Ile Cys Ile Pro Asn Asn Gly Asp Ala Cys Phe Cys Met Lys Trp Leu
 65                  70                  75                  80 aag tcc aag ggt tca cct gta gcg ctg aag atg gcc aac gcg cta cag        288
Lys Ser Lys Gly Ser Pro Val Ala Leu Lys Met Ala Asn Ala Leu Gln
                     85                  90                  95 tgg gcg gcc ttc gct ttg tcg gtc ata atc ctc atc tac tat gca tac        336
Trp Ala Ala Phe Ala Leu Ser Val Ile Ile Leu Ile Tyr Tyr Ala Tyr
                100                 105                 110 gcg acc tgg aga acc acc tgc ggc tgg gag gag gta tat gtg tgc tgc        384
Ala Thr Trp Arg Thr Thr Cys Gly Trp Glu Glu Val Tyr Val Cys Cys
            115                 120                 125 gtc gag ttg acc aag gtc gtg atc gag ttc ttc cac gag ttt gac gag        432
Val Glu Leu Thr Lys Val Val Ile Glu Phe Phe His Glu Phe Asp Glu
130                 135                 140 ccc ggc atg ctg tac ctt gcg aac ggc aac cga gtg ctg tgg ctg cgg        480
Pro Gly Met Leu Tyr Leu Ala Asn Gly Asn Arg Val Leu Trp Leu Arg
145                 150                 155                 160 tac ggc gag tgg ttg ctg acc tgc ccc gtc att ctc atc cac ttg tcc        528
Tyr Gly Glu Trp Leu Leu Thr Cys Pro Val Ile Leu Ile His Leu Ser
                165                 170                 175 aat ttg act ggc ctc aag gac gac tac aac aag cgg acc atg cgg ttg        576
Asn Leu Thr Gly Leu Lys Asp Asp Tyr Asn Lys Arg Thr Met Arg Leu
                180                 185                 190 ctt gtc tcc gat gtc ggc acc atc gtg tgg ggt gct act gcg gcc atg        624
Leu Val Ser Asp Val Gly Thr Ile Val Trp Gly Ala Thr Ala Ala Met
            195                 200                 205 tcc act ggc tac ata aaa gtg att ttc ttc ctc ctc ggt tgc atg tac        672
Ser Thr Gly Tyr Ile Lys Val Ile Phe Phe Leu Leu Gly Cys Met Tyr
210                 215                 220 ggc gca aac aca ttc ttc cac gcc gcc aag gtg tat att gag tcg tac        720
Gly Ala Asn Thr Phe Phe His Ala Ala Lys Val Tyr Ile Glu Ser Tyr
225                 230                 235                 240 cac acc gtc ccc aag ggt ctg tgt cgt cag ctg gtc cgc gcc atg gcc        768
His Thr Val Pro Lys Gly Leu Cys Arg Gln Leu Val Arg Ala Met Ala
                245                 250                 255 tgg ctg ttc ttc gtg tca tgg ggg atg ttt ccc gta ctg ttc ctg ttg        816
Trp Leu Phe Phe Val Ser Trp Gly Met Phe Pro Val Leu Phe Leu Leu
                260                 265                 270 ggg ccc gag ggc ttc gga cat ctg agc gtc tac ggg tca aca atc ggt        864
Gly Pro Glu Gly Phe Gly His Leu Ser Val Tyr Gly Ser Thr Ile Gly
            275                 280                 285 cac acc att atc gac ctt ctc tcc aag aac tgc tgg ggt ctg ctg ggc        912
His Thr Ile Ile Asp Leu Leu Ser Lys Asn Cys Trp Gly Leu Leu Gly
290                 295                 300 cac ttc ctc cgc ctg aag att cac gag cac att ctg ctg tat ggc gat        960
His Phe Leu Arg Leu Lys Ile His Glu His Ile Leu Leu Tyr Gly Asp
305                 310                 315                 320 atc cgc aag gtt cag aag atc agg gtg gcc ggt gag gag ctg gag gtg       1008
Ile Arg Lys Val Gln Lys Ile Arg Val Ala Gly Glu Glu Leu Glu Val
                325                 330                 335 gag acc ctc atg acg gag gag gcc ccc                                   1035
Glu Thr Leu Met Thr Glu Glu Ala Pro
                340                 345
```

```
<210> SEQ ID NO 8
<211> LENGTH: 345
<212> TYPE: PRT
<213> ORGANISM: Artificial
<220> FEATURE:
<223> OTHER INFORMATION: Fusion protein having transmembrane domains of
      volvox channel rhodopsin-2 and the N-terminus region of
      chamydomonas channel rhodopsin-1

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Asp Ala Cys Phe Cys Met Lys Trp Leu
65                  70                  75                  80

Lys Ser Lys Gly Ser Pro Val Ala Leu Lys Met Ala Asn Ala Leu Gln
                85                  90                  95

Trp Ala Ala Phe Ala Leu Ser Val Ile Ile Leu Ile Tyr Tyr Ala Tyr
            100                 105                 110

Ala Thr Trp Arg Thr Thr Cys Gly Trp Glu Glu Val Tyr Val Cys Cys
        115                 120                 125

Val Glu Leu Thr Lys Val Val Ile Glu Phe Phe His Glu Phe Asp Glu
    130                 135                 140

Pro Gly Met Leu Tyr Leu Ala Asn Gly Asn Arg Val Leu Trp Leu Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Asn Lys Arg Thr Met Arg Leu
            180                 185                 190

Leu Val Ser Asp Val Gly Thr Ile Val Trp Gly Ala Thr Ala Ala Met
        195                 200                 205

Ser Thr Gly Tyr Ile Lys Val Ile Phe Phe Leu Leu Gly Cys Met Tyr
    210                 215                 220

Gly Ala Asn Thr Phe Phe His Ala Ala Lys Val Tyr Ile Glu Ser Tyr
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Leu Ser Val Tyr Gly Ser Thr Ile Gly
        275                 280                 285

His Thr Ile Ile Asp Leu Leu Ser Lys Asn Cys Trp Gly Leu Leu Gly
    290                 295                 300

His Phe Leu Arg Leu Lys Ile His Glu His Ile Leu Leu Tyr Gly Asp
305                 310                 315                 320

Ile Arg Lys Val Gln Lys Ile Arg Val Ala Gly Glu Glu Leu Glu Val
                325                 330                 335

Glu Thr Leu Met Thr Glu Glu Ala Pro
            340                 345

<210> SEQ ID NO 9
```

```
<211> LENGTH: 1032
<212> TYPE: DNA
<213> ORGANISM: Artificial
<220> FEATURE:
<223> OTHER INFORMATION: DNA encoding a fusion protein having
      transmembrane domains of volvox channel rhodopsin-1 and the
      N-terminus region of chamydomonas channel rhodopsin-1
<220> FEATURE:
<221> NAME/KEY: CDS
<222> LOCATION: (1)..(1032)

<400> SEQUENCE: 9 atg tcg cgg agg cca tgg ctt ctt gcc cta gcg ctg gca gtg gcg ctg       48
Met Ser Arg Arg Pro Trp Leu Leu Ala Leu Ala Leu Ala Val Ala Leu
1               5                   10                  15 gcg gcc ggc agc gca gga gcc tcg act ggc agt gac gcg acg gtg ccg       96
Ala Ala Gly Ser Ala Gly Ala Ser Thr Gly Ser Asp Ala Thr Val Pro
            20                  25                  30 gtc gcg act cag gat ggc ccc gac tac gtt ttc cac cgt gcc cac gag      144
Val Ala Thr Gln Asp Gly Pro Asp Tyr Val Phe His Arg Ala His Glu
        35                  40                  45 cga atg ctc ttc caa acc tca tac act ctt gag aac aat ggt tct gtt      192
Arg Met Leu Phe Gln Thr Ser Tyr Thr Leu Glu Asn Asn Gly Ser Val
    50                  55                  60 att tgc atg cca aga gga cag tgt tac tgt gaa ggt tgg ctt cgg agt      240
Ile Cys Met Pro Arg Gly Gln Cys Tyr Cys Glu Gly Trp Leu Arg Ser
65                  70                  75                  80 cgc ggc act tcc att gaa aag aca ata gca att act ctt cag tgg gta      288
Arg Gly Thr Ser Ile Glu Lys Thr Ile Ala Ile Thr Leu Gln Trp Val
                85                  90                  95 gtc ttt gct ttg tca gtg gct tgc ctg ggg tgg tat gcg tat caa gcg      336
Val Phe Ala Leu Ser Val Ala Cys Leu Gly Trp Tyr Ala Tyr Gln Ala
            100                 105                 110 tgg cga gct acc tgc gga tgg gag gag gtt tac gta gcc ttg ata gaa      384
Trp Arg Ala Thr Cys Gly Trp Glu Glu Val Tyr Val Ala Leu Ile Glu
        115                 120                 125 atg atg aaa agc atc atc gag gcc ttc cac gag ttc gac agc cct gca      432
Met Met Lys Ser Ile Ile Glu Ala Phe His Glu Phe Asp Ser Pro Ala
    130                 135                 140 aca ctg tgg ctg tct tca ggg aac ggc gta gtt tgg atg cgg tat ggc      480
Thr Leu Trp Leu Ser Ser Gly Asn Gly Val Val Trp Met Arg Tyr Gly
145                 150                 155                 160 gaa tgg ctc ctc acc tgc ccg gtc ctt ctg atc cat ctg agc aac ctc      528
Glu Trp Leu Leu Thr Cys Pro Val Leu Leu Ile His Leu Ser Asn Leu
                165                 170                 175 aca ggc ctg aag gac gat tat agc aaa agg act atg ggc ctg ttg gtt      576
Thr Gly Leu Lys Asp Asp Tyr Ser Lys Arg Thr Met Gly Leu Leu Val
            180                 185                 190 tct gat gtg gga tgc atc gtg tgg ggc gca acc agc gcc atg tgt acg      624
Ser Asp Val Gly Cys Ile Val Trp Gly Ala Thr Ser Ala Met Cys Thr
        195                 200                 205 ggg tgg acg aag atc ctg ttc ttc ctc atc tca ttg agc tat ggt atg      672
Gly Trp Thr Lys Ile Leu Phe Phe Leu Ile Ser Leu Ser Tyr Gly Met
    210                 215                 220 tat acc tat ttt cat gct gct aaa gtt tat atc gaa gca ttc cac aca      720
Tyr Thr Tyr Phe His Ala Ala Lys Val Tyr Ile Glu Ala Phe His Thr
225                 230                 235                 240 gtt cca aaa ggg att tgt cga gaa ctg gtc cga gtg atg gcc tgg aca      768
Val Pro Lys Gly Ile Cys Arg Glu Leu Val Arg Val Met Ala Trp Thr
                245                 250                 255 ttc ttt gtg gct tgg gga atg ttt cca gtc ctg ttt ctg ctg ggc acg      816
Phe Phe Val Ala Trp Gly Met Phe Pro Val Leu Phe Leu Leu Gly Thr
            260                 265                 270
```

```
gaa gga ttc ggt cat atc agc cct tat gga tct gcc att ggg cac tcc      864
Glu Gly Phe Gly His Ile Ser Pro Tyr Gly Ser Ala Ile Gly His Ser
            275                 280                 285 atc ctc gac ctg att gca aag aac atg tgg ggt gtg ctg ggg aat tac      912
Ile Leu Asp Leu Ile Ala Lys Asn Met Trp Gly Val Leu Gly Asn Tyr
        290                 295                 300 ctg cgc gtc aaa atc cac gag cac atc ctg ttg tat ggc gac atc aga      960
Leu Arg Val Lys Ile His Glu His Ile Leu Leu Tyr Gly Asp Ile Arg
305                 310                 315                 320 aag aag cag aaa att acg atc gcc ggc caa gag atg gag gtt gag aca     1008
Lys Lys Gln Lys Ile Thr Ile Ala Gly Gln Glu Met Glu Val Glu Thr
                325                 330                 335 ctg gtg gct gaa gag gag gac cgg                                     1032
Leu Val Ala Glu Glu Glu Asp Arg
            340

<210> SEQ ID NO 10
<211> LENGTH: 344
<212> TYPE: PRT
<213> ORGANISM: Artificial
<220> FEATURE:
<223> OTHER INFORMATION: Fusion protein having transmembrane domains of
      volvox channel rhodopsin-1 and the N-terminus region of
      chamydomonas channel rhodopsin-1

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65              70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Ser Pro Ala
    130                 135                 140

Thr Leu Trp Leu Ser Ser Gly Asn Gly Val Val Trp Met Arg Tyr Gly
145                 150                 155                 160

Glu Trp Leu Leu Thr Cys Pro Val Leu Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe His Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255
```

```
Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
        275                 280                 285

Ile Leu Asp Leu Ile Ala Lys Asn Met Trp Gly Val Leu Gly Asn Tyr
        290                 295                 300

Leu Arg Val Lys Ile His Glu His Ile Leu Leu Tyr Gly Asp Ile Arg
305                 310                 315                 320

Lys Lys Gln Lys Ile Thr Ile Ala Gly Gln Glu Met Glu Val Glu Thr
                325                 330                 335

Leu Val Ala Glu Glu Asp Arg
            340
```

LIGHT-RECEIVING CHANNEL RHODOPSIN HAVING IMPROVED EXPRESSION EFFICIENCY

TECHNICAL FIELD

The present invention relates to a modified light-receiving channel rhodopsin and specifically to a Volvox-derived light-receiving channel rhodopsin which is improved in the expression efficiency on a cell membrane.

BACKGROUND ART

The annual number of people becoming blindness in Japan reaches 16,000 and the causes thereof are broadly divided into two categories: the damage of the inner retinal layer and the damage of the outer retinal layer thereof, excluding the severe injury thereof. The outer retinal layer is known to be selectively degenerated in diseases such as retinitis pigmentosa and age-related macular degeneration.

Taking a look at the light reception of the retina and the signaling mechanism therein, the entered light and image information are received by photoreceptor cells (visual cells) located in the outer retinal layer, and transferred to the inner retinal layer. The information is transferred to the brain through ganglion cells constituting the optic nerve, located in the inner retinal layer. The cells thus capable of receiving light, or an image, are only visual cells in the retina; the degeneration or disappearance of visual cells for any cause will result in the loss of vision even when the other cells are normal.

According to a phototransduction pathway of visual cells, a chain reaction of various proteins is known to be necessary after the reception of light by a light-receiving protein present in the visual cells. Due to such a pathway, it has conventionally been considered that the introduction of a single gene cannot impart the ability to receive light. In this connection, it is reported that the impartment of the ability to receive light to nerve cells requires the introduction of at least 3 proteins (i.e., arrestin, opsin, and G-protein α-subunit) into one cell (Non Patent Literature 1).

Nagel et al. (Non Patent Literature 2) reported that channel rhodopsin-2 (hereinafter also referred to as "ChR2") isolated from green alga Chamydomonas having the ability to receive light and cation-selective permeability and that the introduction of ChR2 gene could give the ability to receive light to cultured mammalian cells (HEK293 and BHK) and the like.

The present inventors reported that when rats with genetic blindness due to the damage of the outer retinal layer were attempted to be subjected to the introduction of channel rhodopsin-2 gene into the remaining neural retina cells to reconstruct visual function, no response (visual evoked potential) of the visual cortex to light was observed before the gene introduction, while the response thereof to light was observed after the gene introduction, and that the lowest illuminance at which the response of the visual cortex was observed was 240 lux in the rats, showing that their retina had a low light sensitivity compared to the normal retina (Non Patent Literature 3).

Thus, the light-receiving protein found in green algae is expected to be applied for vision. However, Chamydomonas-derived ChR2 has light sensitivity limited to a blue color; thus, only blue color can be seen even when vision has been restored.

A similar gene having sensitivity to a red color was found in green alga Volvox (Non Patent Literature 4); however, it is poor in the expression efficiency on a cell membrane and functionally insufficient when expressed in mammalian cells.

CITATION LIST

Patent Literature

Patent Literature 1: JP Patent Publication No. 2006-217866

Non Patent Literature

Non Patent Literature 1: Zemelman BV et al., Neuron, 2002 Jan 3; 33(1): 15-22
Non Patent Literature 2: Nagel G et al., Proc. Natl. Acad. Sci. U S A. 2003 Nov 25; 100(24): 13940-5
Non Patent Literature 3: Tomita H. et al., Invest. Ophthalmol. Vis. Sci., 48 (8): 3821-6, 2007
Non Patent Literature 4: Freng Zhang et al., Nature Neuroscience, Volume 11, Number 6, June 2008: p631-633

SUMMARY OF INVENTION

Accordingly, an object of the present invention is to provide a Volvox-derived light-receiving channel rhodopsin which is improved in the expression efficiency on a cell membrane.

As a result of intensive studies for solving the above problems, the present inventors have found that an N-terminal region of Chlamydomonas reinhardtii-derived channel rhodopsin-1 can be fused to a Volvox-derived channel rhodopsin to improve the expression efficiency of the channel rhodopsin on a cell membrane, thereby accomplishing the present invention.

(1) A modified Volvox carteri-derived light-receiving channel rhodopsin protein, wherein the protein is modified to contain an N-terminal region of Chlamydomonas reinhardtii-derived channel rhodopsin-1 at the N-terminal of a Volvox carteri-derived light-receiving channel rhodopsin protein, wherein the N-terminal region is involved in cell membrane-localized expression and contains no transmembrane domain of the Chlamydomonas reinhardtii-derived channel rhodopsin-1.

(2) The protein according to (1) above, wherein an N-terminal region of the Volvox carteri-derived light-receiving channel rhodopsin is substituted by the corresponding N-terminal region of the Chlamydomonas reinhardtii-derived channel rhodopsin-1.

(3) The protein according to (1) above, wherein the N-terminal region contains at least amino acids 1 to 66 or 1 to 71 of the amino acid sequence shown in SEQ ID NO: 2.

(4) The protein according to (1) above, wherein the protein is any of (a) to (c) below:
(a) a protein consisting of the amino acid sequence shown in SEQ ID NO: 8;
(b) a protein consisting of an amino acid sequence in which one or several amino acids are deleted, substituted, added, or inserted in the amino acid sequence shown in SEQ ID NO: 8 and having biological activities equivalent to or higher than those of the polypeptide of (a); and
(c) a protein consisting of an amino acid sequence having at least 90% sequence identity to the amino acid sequence shown in SEQ ID NO: 8 and having biological activities equivalent to or higher than those of the polypeptide of (a).

(5) The protein according to (1) above, wherein the protein is any of (a) to (c) below:

(a) a protein consisting of the amino acid sequence shown in SEQ ID NO: 10;
(b) a protein consisting of an amino acid sequence in which one or several amino acids are deleted, substituted, added, or inserted in the amino acid sequence shown in SEQ ID NO: 10 and having biological activities equivalent to or higher than those of the polypeptide of (a); and
(c) a protein consisting of an amino acid sequence having at least 90% sequence identity to the amino acid sequence shown in SEQ ID NO: 10 and having biological activities equivalent to or higher than those of the polypeptide of (a).

(6) The protein according to any one of (1) to (5) above, wherein the protein further contains a fluorescent protein at the C-terminal.

(7) A polynucleotide encoding the protein according to any one of (1) to (6) above.

(8) An expression vector comprising the polynucleotide according to (7) above functionally linked to a promoter.

(9) A cell expressing the protein according to any one of (1) to (6) above.

(10) The cell according to (9) above, wherein the cell is a visual cell.

(11) Use of the protein according to any one of (1) to (6) above, the polynucleotide according to (7) above, or the expression vector according to (8) above in the production of a pharmaceutical for treating a subject suffering from damage of the external layer of the retina.

(12) The use according to (11) above, wherein the damage of the external layer of the retina is retinal pigmentary degeneration, age-related macular degeneration, or retinal detachment.

(13) A pharmaceutical composition for treating the damage of the external layer of the retina, comprising the protein according to any one of (1) to (6) above, the polynucleotide according to (7) above, or the expression vector according to (8) above as an active ingredient.

(14) The pharmaceutical composition according to (13) above, wherein the damage of the external layer of the retina is retinal pigmentary degeneration, age-related macular degeneration, or retinal detachment.

According to the present invention, a Volvox-derived light-receiving channel rhodopsin is provided which is improved in the expression efficiency on a cell membrane.

The light-receiving channel rhodopsin according to the present invention has sensitivity to yellow light to red light, preferably blue light to red light, and can be used, for example, for reconstructing mammalian visual function, because it shows efficient cell membrane-localized expression.

The present specification encompasses the contents of the specification and/or drawings of Japanese Patent Application No. 2009-185455 on which the priority of the present application is based.

BRIEF DESCRIPTION OF DRAWINGS

The patent or application file contains at least one color drawing. Copies of this patent or patent application publication with color drawing will be provided by the USPTO upon request and payment of the necessary fee.

FIG. 2 is a pair of diagrams showing nucleotide sequences of ChR-HSB (left)(SEQ ID NO: 7) and hChR-YR (right) (SEQ ID NO: 9). The underlined portions indicate the portions of sequences of Chlamydomonas ChR1.

DESCRIPTION OF EMBODIMENTS

Figure 1:
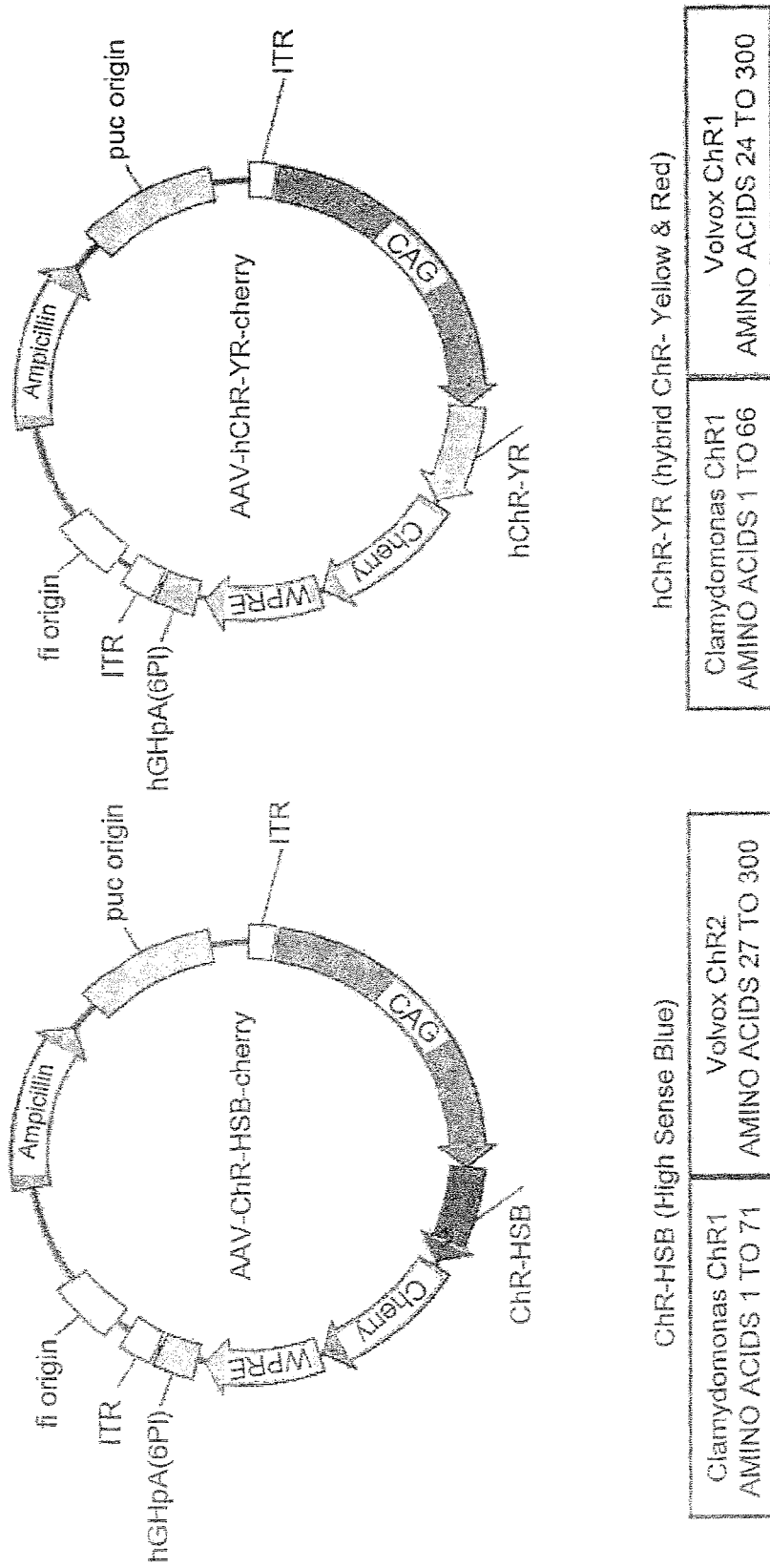
FIG. 1 is a pair of diagrams showing configurations of adenovirus-associated viral vectors for expressing ChR-HSB (left) and hChR-YR (right).

The present invention relates to a modified light-receiving channel rhodopsin derived from Volvox carteri (hereinafter also referred to as a modified rhodopsin protein).

The modified rhodopsin protein according to the present invention is a Volvox carteri-derived channel rhodopsin (hereinafter also referred to as VolChR) which is modified so as to contain an N-terminal region of Chlamydomonas reinhardtii-derived channel rhodopsin-1 (hereinafter also referred to as ChR1) at the N-terminal region, and as a result, characterized by being improved in the expression efficiency on a cell membrane, particularly on a mammalian cell membrane.

1. Modified Rhodopsin Protein 1.1 Volvox Channel Rhodopsin (VolChR)

According to the present invention, any of channel rhodopsin-1 (hereinafter also referred to as VolChR1) and channel rhodopsin-2 (VolChR2) may be used as VolChR. An example of the nucleotide sequence of VolChR1 gene is shown in SEQ ID NO: 3, and the amino acid sequence of VolChR1 encoded by the nucleotide sequence shown in SEQ ID NO: 3 is shown in SEQ ID NO: 4. An example of the nucleotide sequence of VolChR2 gene is shown in SEQ ID NO: 5, and the amino acid sequence of VolChR2 encoded by the nucleotide sequence shown in SEQ ID NO: 5 is shown in SEQ ID NO: 6.

The VolChR used in the present invention is not limited to the polypeptide consisting of the amino acid sequence shown in SEQ ID NO: 4 or 6, and includes a polypeptide in which one or a plurality of amino acids is substituted, deleted, added, or inserted in the amino acid sequence shown in SEQ ID NO: 4 or 6 and which has biological activities equivalent to or higher than those of VolChR1 or VolChR2 consisting of the amino acid sequence shown in SEQ ID NO: 4 or 6, or a polypeptide which has a sequence substantially identical to the amino acid sequence shown in SEQ ID NO: 4 or 6 and has biological activities equivalent to or higher than those of VolChR1 or VolChR2 consisting of the amino acid sequence shown in SEQ ID NO: 4 or 6 (hereinafter also referred to as "VolChR mutant polypeptide").

"A plurality of" used herein in relation to the VolChR mutant polypeptide is an integer of 50 or less, preferably an integer of 30 or less, more preferably an integer of 10 or less, and, for example, 2 to 9, 2 to 7, or 2 to 5.

The "substantially identical sequence" refers to a sequence having at least 90%, more preferably at least 95%, still more preferably at least 96%, 97%, 98%, or 99% sequence identity to the amino acid sequence shown in SEQ ID NO: 4 or 6. In this respect, % identity refers to a value calculated using a software for calculating the identity between a plurality of (two) amino acid sequences (e.g., FASTA, DANASYS, and BLAST) with default settings.

"Equivalent biological activities" used herein in relation to the VolChR mutant polypeptide refers to the intensities of biological activities such as light sensitivity and channel function being each substantially the same. This term may also include the case where they have biological activities of substantially the same quality, and biological activities of "the same quality" as employed herein refer to light reception wavelength and, for example, the property of an ion permeation activity being each the same.

The VolChR gene is not limited to the polynucleotide consisting of the nucleotide sequence shown in SEQ ID NO: 3 or 5 and includes a polynucleotide capable of hybridizing to a complementary strand of the polynucleotide consisting of the nucleotide sequence shown in SEQ ID NO: 3 or 5 under stringent conditions and encoding a polypeptide having biological activities equivalent to or higher than those of VolChR consisting of the amino acid sequence shown in SEQ ID NO: 4 or 6 (hereinafter also referred to as "VolChR mutant polynucleotide"), and a polynucleotide having at least 90%, more preferably at least 95%, 96%, 97%, or 98%, most preferably at least 99% sequence identity to the nucleotide sequence shown in SEQ ID NO: 3 or 5 and encoding a polypeptide having biological activities equivalent to or higher than those of VolChR consisting of the amino acid sequence shown in SEQ ID NO: 4 or 6 (hereinafter also referred to as "VolChR mutant polynucleotide").

As used herein, "stringent conditions" include, but not limited to, for example, hybridization in 3 to 4×SSC (150 mM sodium chloride, 15 mM sodium citrate, pH 7.2) and 0.1 to 0.5% SDS at 30° C. to 50° C. for 1 to 24 hours, more preferably hybridization in 3.4×SSC and 0.3% SDS at 40° C. to 45° C. for 1 to 24 hours, and subsequent washing. Examples of washing conditions can include conditions such as washing with a solution containing 2×SSC and 0.1% SDS, or continuous washing with a 1×SSC solution and a 0.2×SSC solution at room temperature. However, the combination in the above conditions is exemplary, and one of ordinary skill in the art can achieve the same stringency as that described above by properly combining the above or other factors determining hybridization stringency (for example, the concentration, length, and GC content of a hybridization probe, the reaction time of hybridization, etc.).

The VolChR mutant polynucleotide may be a naturally occurring one or one in which the mutation is artificially introduced. The artificial mutation can be introduced by an ordinary method using, for example, a site-directed mutation introduction method, a mutation introduction method utilizing PCR, or the like (Proc. Natl. Acad. Sci. USA., 1984, 81: 5662; Sambrook et al., Molecular Cloning A Laboratory Manual (1989) Second edition, Cold Spring Harbor Laboratory Press; Ausubel et al., Current Protocols in Molecular Biology 1995 John Wiley & Sons).

Whether the VolChR mutant polypeptide or the polypeptide encoded by the VolChR mutant polynucleotide described above has biological activities equivalent to those of VolChR or not can be assayed, for example, by examining a membrane potential record using an electrophysiological technique or a change in the intracellular ion concentration using a fluorescent probe.

According to the present invention, it is not always necessary to use the full length of VolChR as VolChR; a VolChR fragment may be used provided that it retains the 7-transmembrane spanning domain responsible for light sensitivity and channel function. Examples of the VolChR fragment can include, but not limited to, amino acids 24 to 300 of the amino acid sequence shown in SEQ ID NO: 4 and amino acids 27 to 300 of the amino acid sequence shown in SEQ ID NO: 6.

1.2 N-Terminal Region of Chlamydomonas Channel Rhodopsin-1 (ChR1)

An example of the nucleotide sequence of ChR1 gene is shown in SEQ ID NO: 1, and the amino acid sequence of ChR1 encoded by the nucleotide sequence shown in SEQ ID NO: 1 is shown in SEQ ID NO: 2.

The present invention is based partly on the finding that the N-terminal region of ChR1 is involved in localized expression on a cell membrane, particularly on a mammalian cell membrane. Thus, the term "N-terminal region of ChR1" as used herein refers to the N-terminal region of ChR1 imparting the cell membrane-localized expression to VolChR and is characterized by not containing the deduced transmembrane domain of ChR1. Specifically, the N-terminal region of ChR1 is a polypeptide consisting of amino acids 1-to-83 of the amino acid sequence shown in SEQ ID NO: 2 (hereinafter also referred to as 1-to-83 polypeptide) or a mutant thereof (hereinafter also referred to as mutant 1-to-83 polypeptide), or a fragment thereof. As used herein, "imparting the cell membrane-localized expression" refers to, for example, increased expression on a cell membrane or improved function as a membrane protein compared to those of VolChR not containing the N-terminal region of the ChR1 described above.

The mutant 1-to-83 polypeptide includes a polypeptide in which one or a plurality of amino acids is substituted, deleted, added, or inserted in the above 1-to-83 polypeptide and which has biological activities equivalent to or higher than those of the above 1-to-83 polypeptide, or a polypeptide which has a sequence substantially identical to that of 1-to-83 polypeptide and has biological activities equivalent to or higher than those of 1-to-83 polypeptide.

"Several" used herein in relation to the mutant 1-to-83 polypeptide refers to an integer of 10 or less, preferably an integer of 5 or less and, for example, 4, 3, or 2.

The "substantially identical sequence" refers to a sequence having at least 90%, more preferably at least 95%, still more preferably at least 96%, 97%, 98%, or 99% sequence identity to 1-to-83 polypeptide. In this respect, % identity refers to a value calculated using a software for calculating the identity between a plurality of (two) amino acid sequences (e.g., FASTA, DANASYS, and BLAST) with default settings.

"Equivalent biological activities" used herein in relation to the mutant 1-to-83 polypeptide refers to showing cell membrane-localized expression comparable to that of 1-to-83 polypeptide when fused to VolChR, for example.

The coding gene for 1-to-83 polypeptide is not limited to the polynucleotide consisting of nucleotides 98 to 346 shown in SEQ ID NO: 1 (hereinafter also referred to as 98-to-346 polynucleotide) and includes a polynucleotide capable of hybridizing to a complementary strand of the 98-to-346 polynucleotide under stringent conditions and encoding a polypeptide having biological activities equivalent to or higher than those of 1-to-83 polypeptide (hereinafter also referred to as "mutant 98-to-346 polynucleotide").

As used herein, "stringent conditions" include, but not limited to, for example, hybridization in 3 to 4×SSC (150 mM sodium chloride, 15 mM sodium citrate, pH 7.2) and 0.1 to 0.5% SDS at 30° C. to 50° C. for 1 to 24 hours, more preferably hybridization in 3.4×SSC and 0.3% SDS at 40° C. to 45° C. for 1 to 24 hours, and subsequent washing. Examples of washing conditions can include conditions such as washing with a solution containing 2×SSC and 0.1% SDS, or continuous washing with a 1×SSC solution and a 0.2×SSC solution at room temperature. However, the combination in the above conditions is exemplary, and one of ordinary skill in the art can achieve the same stringency as that described above by properly combining the above or other factors determining hybridization stringency (for example, the concentration, length, and GC content of a hybridization probe, the reaction time of hybridization, etc).

The mutant 98-to-346 polynucleotide may be a naturally occurring one or one in which the mutation is artificially introduced. The artificial mutation can be introduced by an ordinary method using, for example, a site-directed mutation introduction method, a mutation introduction method utilizing PCR or the like (Proc. Natl. Acad. Sci. USA., 1984, 81: 5662; Sambrook et al., Molecular Cloning A Laboratory Manual (1989) Second edition, Cold Spring Harbor Laboratory Press; Ausubel et al., Current Protocols in Molecular Biology 1995 John Wiley & Sons).

The fragment of 1-to-83 polypeptide or the mutant 1-to-83 polypeptide may be any fragment provided that it can impart cell membrane-localized expression to VolChR. Preferably, the fragment contains at least amino acids 1 to 66 or 1 to 71 of the amino acid sequence shown in SEQ ID NO: 2.

Whether the mutant 1-to-83 polypeptide, the polypeptide encoded by the mutant 98-to-346 polynucleotide, or the fragment of 1-to-83 polypeptide has biological activities equivalent to 1-to-83 polypeptide or not can be determined, for example, by expressing VolChR containing each of the polypeptides and the fragment at the N-terminal as a fused protein with a fluorescent protein in cells (e.g., in mammalian cells) and visually identifying the degree of expression on a cell membrane.

1.3 Modified Rhodopsin Protein

The modified rhodopsin protein according to the present invention is a fused polypeptide containing an N-terminal region of ChR1 at the N-terminal of VolChR.

The modified rhodopsin protein may be one in which the N-terminal region of ChR1 is simply added to the N-terminal of VolChR, or one in which the N-terminal of VolChR is substituted by the N-terminal region of ChR1.

When the modified rhodopsin protein according to the present invention is one in which the N-terminal of VolChR is substituted by the N-terminal region of ChR1, the N-terminal region of VolChR to be substituted is not particularly limited provided that the 7-transmembrane spanning domain of VolChR is conserved. Thus, when VolChR1 is used, all or part of amino acids 1 to 23 of the amino acid sequence shown in SEQ ID NO: 4 may be substituted with the N-terminal region of ChR1; similarly, when VolChR2 is used, all or part of amino acids 1 to 26 of the amino acid sequence shown in SEQ ID NO: 6 may be substituted with the N-terminal region of ChR1.

Preferred examples of the modified rhodopsin protein of the present invention produced as described above can include the polypeptide consisting of the amino acid sequence shown in SEQ ID NO: 8 or 10 (herein also referred to as ChR-HSB or hChR-YR, respectively), or a functional equivalent thereof. Examples of the functional equivalent of ChR-HSB or hChR-YR include a polypeptide in which one or several amino acids is deleted, substituted, added, or inserted in the amino acid sequence of ChR-HSB or hChR-YR or which has at least 90%, preferably at least 95%, 96%, 97%, or 98%, most preferably 99% sequence identity to the amino acid sequence of ChR-HSB or hChR-YR and which has biological activities equivalent to or higher than those of ChR-HSB or hChR-YR. In this respect, "several" as employed herein is an integer of 30 or less, preferably an integer of 10 or less, and, for example, 2 to 9, 2 to 7, or 2 to 5, and % sequence identity refers to a value calculated using a software for calculating the identity between a plurality of (two) amino acid sequences (e.g., FASTA, DANASYS, and BLAST) with default settings.

"Equivalent biological activities" used in relation to the modified rhodopsin protein of the present invention refers to the intensities of biological activities such as light sensitivity, channel function, and cell membrane-localized expression being each substantially the same.

The modified rhodopsin protein of the present invention may preferably contain a fluorescent protein at the C-terminal. As used herein, the "fluorescent protein" is any fluorescent protein which emits light having sensing wavelengths of VolChR when excited by visible light (i.e., light at a wavelength of 390 nm to 770 nm) or emits light having sensing wavelengths of VolChR with a change in the ion concentration. The presence of the fluorescent protein enables VolChR to receive light emitted by the fluorescent protein as well as directly incident light and thus can increase the light reception amount of VolChR with a lower illuminance.

Examples of the fluorescent protein which may be used in the present invention can include, but not limited to, a cyan fluorescent protein, a green fluorescent protein, a yellow fluorescent protein, and DsRed.

1.4 Preparation of Modified Rhodopsin Protein

The modified rhodopsin protein of the present invention can be produced by a genetic engineering technique on the basis of the sequence information of VolChR gene and ChR gene.

Specifically, a polynucleotide encoding the modified rhodopsin protein of the present invention (hereinafter also referred to as "modified rhodopsin gene") is first prepared. The modified rhodopsin gene can be prepared by a technique well known to those of skill in the art. For example, a polynucleotide encoding a desired modified rhodopsin protein can be chemically synthesized based on the sequence information of a VolChR gene and the sequence information of ChR1 gene. Alternatively, it may be prepared by designing and chemically synthesizing PCR primers for amplifying a desired region of the VolChR gene and PCR primers for amplifying a desired region of ChR1 gene on the basis of both the pieces of sequence information, separately amplifying the VolChR gene region and the ChR1 gene region by PCR using a genomic DNA extracted from an organism of interest as a template, and linking these regions.

The modified rhodopsin gene of the present invention functionally linked to a promoter can be then incorporated into an expression vector whose replication can be maintained in host bacterial cells and which can stably express the protein and can stably retain the gene, followed by transforming the host with the resultant recombinant expression vector to produce the modified rhodopsin protein of the present invention in the host. On the recombinant technology, Sambrook et al. (supra) and Ausubel et al. (supra) may be referred to.

Examples of the expression vector which may be used include, but not limited to, Escherichia coli-derived plasmids (e.g., pET28, pGEX4T, pUC118, pUC119, pUC18, pUC19, and other plasmid DNA), *Bacillus subtilis*-derived plasmids (e.g., pUB110, pTP5, and other plasmid DNA), yeast-derived plasmids (e.g., YEp13, YEp24, YCp50, and other plasmid DNA), λ phages (λ gt11, λ ZAP, etc.), plasmids for use in mammals (pCMV, pSV40), viral vectors (animal virus vectors such as adenovirus vector, adeno-associated virus vector, retrovirus vector, lentivirus vector, and vaccinia virus, insect virus vectors such as baculovirus vector, etc.), vectors for use in plants (binary vector pBI, etc.), and cosmid vectors.

As used herein, "functionally linked" refers to such functional linkage between a promoter sequence and a desired polynucleotide sequence that the promoter sequence can start the transcription of the desired polynucleotide sequence.

The promoter is not particularly limited; a suitable promoter may be selected depending on the host, and the promoter may be any of a constitutive promoter and an inducible promoter which are well known in the art. In the present invention, it is particularly preferable to use a constitutive promoter. Examples of the promoter which may be used in the present invention can include CMV promoter, SV40 promoter, CAG promoter, synapsin promoter, rhodopsin promoter, CaMV promoter, glycolytic enzyme promoters, lac promoter, trp promoter, tac promoter, GAPDH promoter, GAL1 promoter, PH05 promoter, PGK promoter, and thy1 promoter.

The insertion of the modified rhodopsin gene into an expression vector is carried out, for example, by creating or linking restriction enzyme sites flanking the modified rhodopsin gene and inserting the resultant into a restriction enzyme site or multicloning site of a suitable vector DNA. In addition to the promoter and the modified rhodopsin gene, the expression vector may contain an enhancer and other cis elements, a splicing signal, a poly A addition signal, a selection marker (a drug resistance gene marker such as an ampicillin resistance marker or a tetracycline resistance marker, an auxotrophic complementary gene marker such as LEU1, TRP1, or URA3, a dominant selection marker such as APH, DHFR, or TK, or the like), a ribosomal binding site (RBS), and the like, if necessary.

The transformation of the host can be carried out using a protoplast method, a spheroplast method, a competent cell method, a virus method, a calcium phosphate method, a lipofection method, a microinjection method, a gene bombardment method, an agrobacterium method, an electroporation method, or the like.

The resultant transformant is cultured under suitable conditions using a medium containing assimilateable carbon and nitrogen sources, metal salts, vitamins, and the like. The culture of the transformant is typically carried out under aerobic conditions such as shake culture or aerated and agitated culture at 25° C. to 37° C. for 3 to 6 hours. The pH is kept around neutrality during the period of culture. The pH is adjusted using an inorganic or organic acid, an alkaline solution, or the like. During the culture, an antibiotic such as ampicillin or tetracycline may be added to the medium depending on the selection marker inserted into the recombinant expression vector, if necessary. The host used for the transformation is not particularly limited provided that it can express the modified rhodopsin protein of the present invention; examples thereof include bacteria (*Escherichia coli, Bacillus subtilis*, etc.), yeasts (*Saccharomyces cerevisiae*, etc.), animal cells (COS cells, Chinese hamster ovary cells (CHO), 3T3 cells, BHK cells, HEK293 cells, etc.), and insect cells.

The modified rhodopsin protein of the present invention can be separated and purified by a common method from a culture (a culture supernatant, cultured cells, cultured bacterial cells, a homogenate of cells or bacterial cells, or the like) obtained by culturing the transformant, and obtained in the form of retaining its activities by ultrafiltration concentration, freeze drying, spray drying, crystallization, or the like. Alternatively, the modified rhodopsin protein of the present invention may be provided in the form of cells expressing the protein without performing isolation or purification. In this case, the host cells used for the transformation are host cells suitable for subsequent use, for example, visual cells, preferably human visual cells.

When the modified rhodopsin protein of the present invention is used for a medical application, it may be provided in the form of a vector for expressing the protein. In this case, an expression vector is preferably used which is excellent in the efficiency of introduction into cells, the maintenance of replication in the cells, stability, the expression efficiency, and the like. Examples of the vector can include, but not limited to, viral vectors such as an adeno-associated vector, a retrovirus vector, and a lentivirus vector, plasmids (capable of independent replication), and transposons.

The vector for expressing the modified rhodopsin protein of the present invention can be produced according to the method described, for example, in Tomita H et al., Invest. Ophthalmol. Vis. Sci. 2007 Aug; 48(8): 3821-6; and Sugano E et al., Invest. Ophthalmol. Vis. Sci. 2005 Sep; 46(9): 3341-8.

2. Therapeutic Application

The modified rhodopsin protein of the present invention is a channel rhodopsin showing efficient localized expression on a cell membrane, particularly on a mammalian cell membrane. The modified rhodopsin protein also retains the light sensitivity and channel function of the Volvox-derived channel rhodopsin having sensitivity to yellow light to red light; thus, it can be used for the construction of visual function capable of recognizing yellow to red colors. Preferably, the modified rhodopsin protein of the present invention has sensitivity to blue light to red light and can be used for the construction of visual function capable of recognizing blue to red colors.

Thus, the modified rhodopsin protein of the present invention and the expression vector containing a polynucleotide encoding the protein are useful for the treatment of a subject suffering from the damage of the external layer of the retina.

"Damage of the outer retinal layer" refers to any disease in which cells other than visual cells remain normal or retain some of their functions although the failure or impairment of visual function occurs as by the degeneration or disappearance of visual cells present in the external layer of the retina. According to the present invention, examples of the disease can include, but not limited to, retinitis pigimentosa, age-related macular degeneration, and retinal detachment.

As used herein, "subject" means a subject losing vision or being at risk of the loss of vision due to the damage of the outer retinal layer. According to the present invention, the subject is not limited to a human and may be any of other mammals. Examples of other mammals include mice, rats, monkeys, rabbits, dogs, cats, cattle, and horses.

As used herein, "treatment of a subject suffering from the damage of the outer retinal layer" refers to recovering visual function compared to before the administration of the pharmaceutical of the present invention in a subject losing vision or being at risk of the loss of vision due to the damage of the outer retinal layer.

The modified rhodopsin protein of the present invention and the vector containing a polynucleotide encoding the protein can be used for the reconstruction of visual function having wider sensitivity to the visual light range by use thereof in combination with another green alga-derived channel rhodopsin having a different light response range (e.g., Chlamydomonas-derived channel rhodopsin-1 or-2), if necessary.

2.1 Pharmaceutical Composition

The pharmaceutical composition of the present invention uses the modified rhodopsin protein of the present invention or the vector containing a polynucleotide encoding the protein as an active ingredient and is formulated as a pharmaceutical for treating a subject suffering from the damage of the external layer of the retina. Thus, the pharmaceutical of the present invention comprises a therapeutically effective dose of the fused protein or the expression vector. "Therapeutically effective dose" refers to a dose capable of providing a therapeutic effect for a given symptom or usage; although the dose is properly determined by one of ordinary skill in the art from the results of a test using an animal and a clinical trial, the age, body weight, and sex of the subject to be administered, the condition or severity of the symptom, the administration method, and the like should be considered. In the case of virus, the viral dose is, for example, $10^{12}$ to $10^{13}$ capsids/ml (e.g., about $10^{13}$ capsids/ml).

In formulating the pharmaceutical of the present invention, the above active ingredient is formulated together with at least one pharmaceutically acceptable carrier. Examples of the pharmaceutically acceptable carrier can include, but not limited to, various buffer solutions such as saline and buffer solutions of phosphates, acetates, or the like.

The pharmaceutical of the present invention may comprise a therapeutic ingredient other than the above ingredient provided that the effect according to the present invention is not impaired. Examples of the therapeutic ingredient include well-known agents as therapeutic agents for retinal pigmentary degeneration, age-related macular degeneration, or retinal detachment.

The pharmaceutical of the present invention can be formulated, for example, into an injection for local administration, or eye drops or eye washes. The preparation for injection can be provided, for example, as an ample or in a unit dosage form in a container for multiple administrations, after adding a preservative. Alternatively, the pharmaceutical of the present invention may be in the form of a freeze dried preparation for reconstitution before use with a suitable vehicle, for example, sterilized water containing no pyrogenic substance.

The pharmaceutical of the present invention is preferably administered by direct injection into the affected area of a subject, i.e., the retina, or direct contact to the vitreous body.

The present invention will be described below in further detail with reference to Examples. However, the present invention is not limited thereto.

EXAMPLE

Construction of ChR-HSB and hChR-YR

ChR-HSB

The region of nucleotides 98 to 309 of Chlamydomonas-derived channel rhodopsin 1 (ChR1; Gene Bank #AF385748) and the region of nucleotides 123 to 945 of Volvox-derived channel rhodopsin 2 (volChR2; EU285660) were amplified by a PCR method and inserted into a multicloning site of a plasmid for preparing an adeno-associated virus vector. The plasmid for preparing an adeno-associated virus vector has a fluorescent protein gene, pmCherry, positioned in the 3' region of the multicloning site, and the target gene is expressed in the form of a fused protein having the fluorescent protein pmCherry at the C-terminal region (FIG. 1 left; AAV-ChR-HSB-Cherry).

hChR-YR

The region of nucleotides 98 to 297 (C at position 244 was substituted with A) of Chlamydomonas-derived channel rhodopsin 1 (ChR1; Gene Bank #AF385748) and the region of nucleotides 72 to 903 of Volvox-derived channel rhodopsin 1 (volChR1;EU622855) were amplified by a PCR method and inserted into a multicloning site of a plasmid for preparing an adeno-associated virus vector. The plasmid for preparing an adeno-associated virus vector has a fluorescent protein gene, pmCherry, positioned in the 3' region of the multicloning site, and the target gene is expressed in the form of a fused protein having the fluorescent protein pmCherry at the C-terminal region (FIG. 1 right; AAV-hChR-YR-Cherry). The nucleotide sequences of ChR-HSB and hChR-YR are shown in FIG. 2.

Preparation of Virus Vector

The virus vector was prepared according to a manual for AAV Helper-Free System (Stratagene Corp, La Jalla, Calif.). Two plasmids (pAAV-RC and pHelper) necessary for the preparation of the virus other than the plasmid containing the target gene (pAAV-ChR-HSB-pmCherry or pAAV-hChR-YR-pmCherry) used were the same plasmids as those in the AAV Helper-Free System.

15 µg each of 3 plasmids (pAAV-ChR-HSB-pmCherry or pAAV-hChR-YR-pmCherry, pAAV-RC, and pHelper) were co-transfected into 293T cells cultured in a 15-cm culture dish by a calcium phosphate method. Specifically, a tube containing the 3 plasmids was subjected to tapping, to which 1.5 ml of 0.3 M $CaCl_2$ was then added, followed by mixing by inversion. These plasmids were added to 1.5 ml of 2X HBS (280 mM NaCl, 1.5 mM $Na_2HPO_4$, 50 mM HEPES, pH7.1) provided in another tube. The resultant was again subjected to inversion stirring and dropwise added to 293T cells. The 293 cells were cultured at 37° C., and the resultant cells were recovered after 3 days. Virus particles were purified from the cells to provide a viral vector.

Identification of Gene Expression Site in Cultured Cell

Human fibrosarcoma cell line HT1080 cultured in a DMEM medium containing 10% fetal bovine serum (FBS) (10% FBS-DMEM) was used to examine the intracellular expression site of the transgene (ChR-HSB or hChR-YR). A virus solution containing ChR-HSB or hChR-YR was diluted 1:100 with a 2% FBS-DMEM medium and cultured for 4 hours for infection. The intracellular localization was observed under a fluorescence microscope 3 days after infection (FIG. 3).

Figure 3:
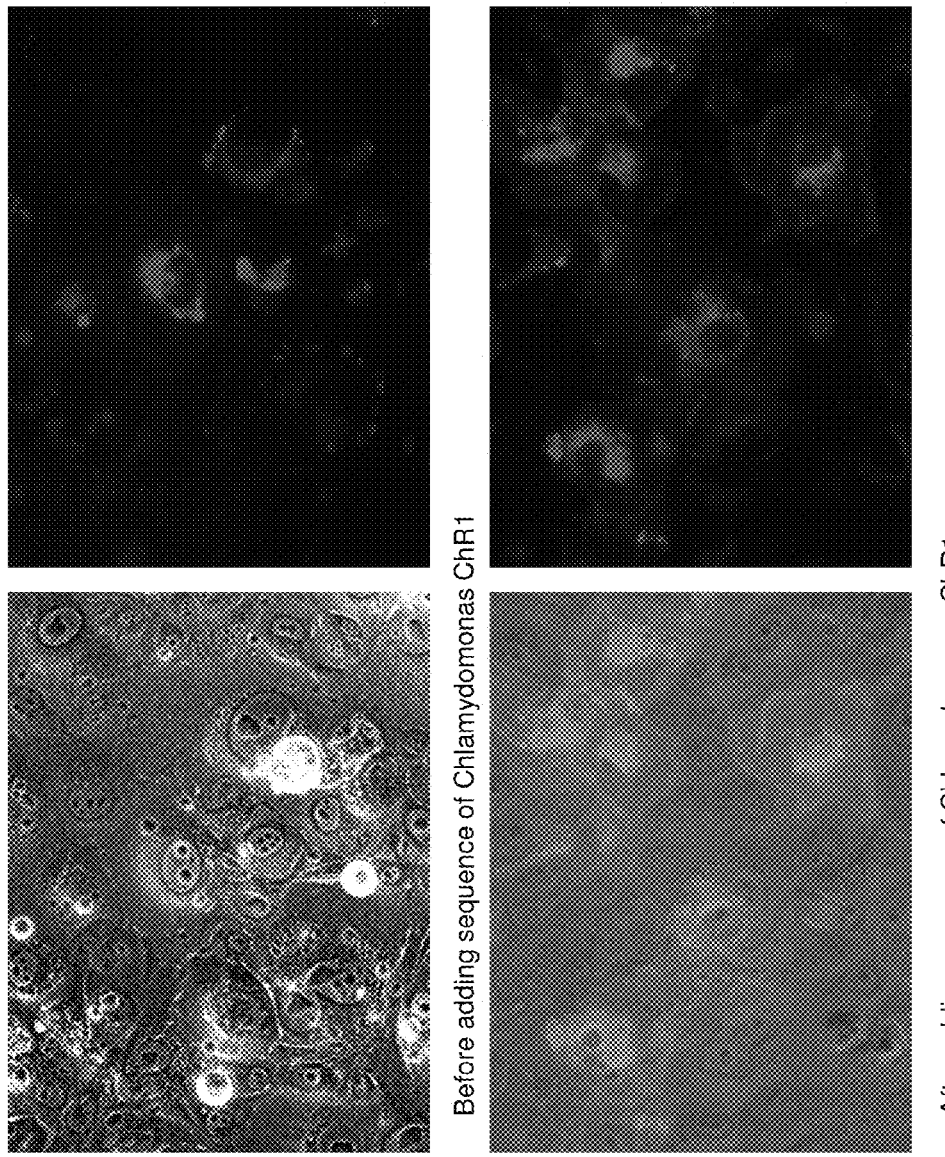
FIG. 3 is a series of photographs showing different expressions of non-modified VolCh and modified VolCh in the human fibrosarcoma cell line HT1080. In the figure, the left photographs show merged images of phase-contrast micrographs and fluorescence micrographs, and the right photographs show fluorescence micrographs.

FIG. 3 shows that while the non-modified VolChR is expressed mainly in the endoplasmic reticulum, the modified VolChR is also expressed in the cytoplasm and the cell membrane. Thus, the addition of the N-terminal region of ChR1 to VolChR was demonstrated to result in an increased expression efficiency of the gene and the expression thereof on the cell membrane.

Experimental Animal 6-month old Royal College of Surgeons (RCS: rdy/rdy) rats were used for the experiment. In RCS rats, the retina is once normally formed after birth, but visual cells start to degenerate from 3 weeks after birth and almost disappear 3 months after birth, leading to the loss of vision. In 6-month old RCS rats, no visual evoked potential is recorded.

Introduction of Gene into Retina

Under mixed anesthesia of ketamine (66 mg/kg) and xylazine (3.3 mg/kg), about 1 mm of the bulbar conjunctiva was cut open, a 32-gauge microsyringe was inserted from the ciliary ring, and 5 µl of the virus solution was injected into the vitreous body. To examine the functional difference between the ChR-HSB now prepared and the Chlamydomonas-derived ChR2 having sensitivity to a blue color already isolated from Chlamydomonas, the virus containing ChR-HSB was administered to one eye and the virus containing Chlamydomonas-derived ChR2 was administered to the opposite eye, followed by measuring the visual evoked potential.

Visually Evoked Potential Measurement

The visually evoked potential was measured 2 months after the virus injection into the vitreous body. The visual evoked potential was measured and recorded using Neuropack (MEB-9102) from Nihon Kohden Corporation. Electrodes for VEP recording were placed on the dura at positions of 6.8 mm from the bregma to the lambda on the median line and 3 mm left and right from the center in a state of the scalp being cut open to expose the cranium. A reference electrode was placed at a position of 12 mm from the bregma to the lambda on the median line. These electrodes placed were fixed using dental cement. Under mixed anesthesia of ketamine (66 mg/kg) and xylazine (3.3 mg/kg), the measurement was carried out in a state of the pupils being dilated using 1% atropine and 2.5% phenylephrine hydrochloride. The visual stimulation used a blue LED as a light source and was repeated 100 times at an irradiation time of 20 ms and a stimulus frequency of 1 Hz for recording by averaging (FIG. 4).

Figure 4:
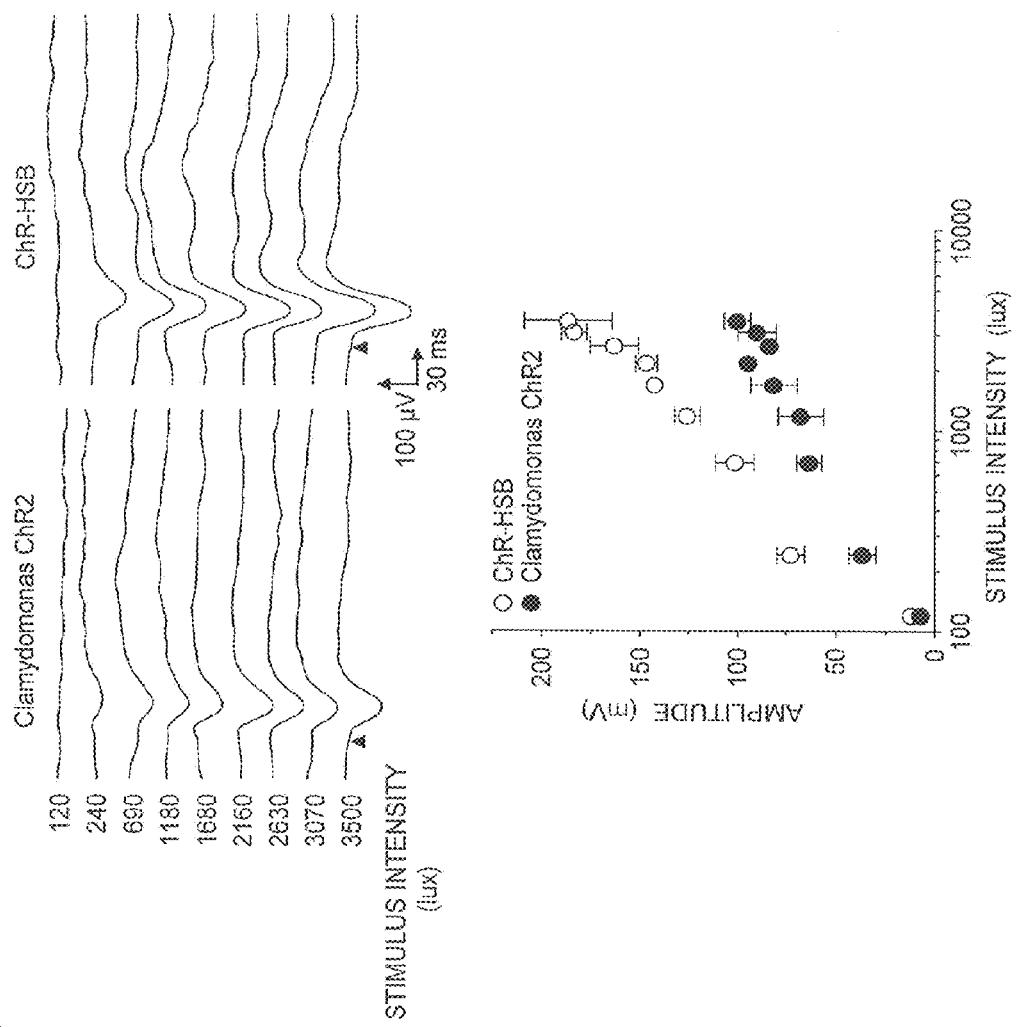
FIG. 4 is a set of drawings showing results of measuring visually evoked potential after introducing Chlamydomonas ChR2 or ChR-HSB.

As shown in FIG. 4, for the eye to which ChR-HSB was administered, a significantly higher amplitude of the visual evoked potential was shown. Thus, ChR-HSB was shown to have high sensitivity compared to Chlamydomonas ChR2.

Preparation of Flat-Mounted Retina Preparation

Figure 5:
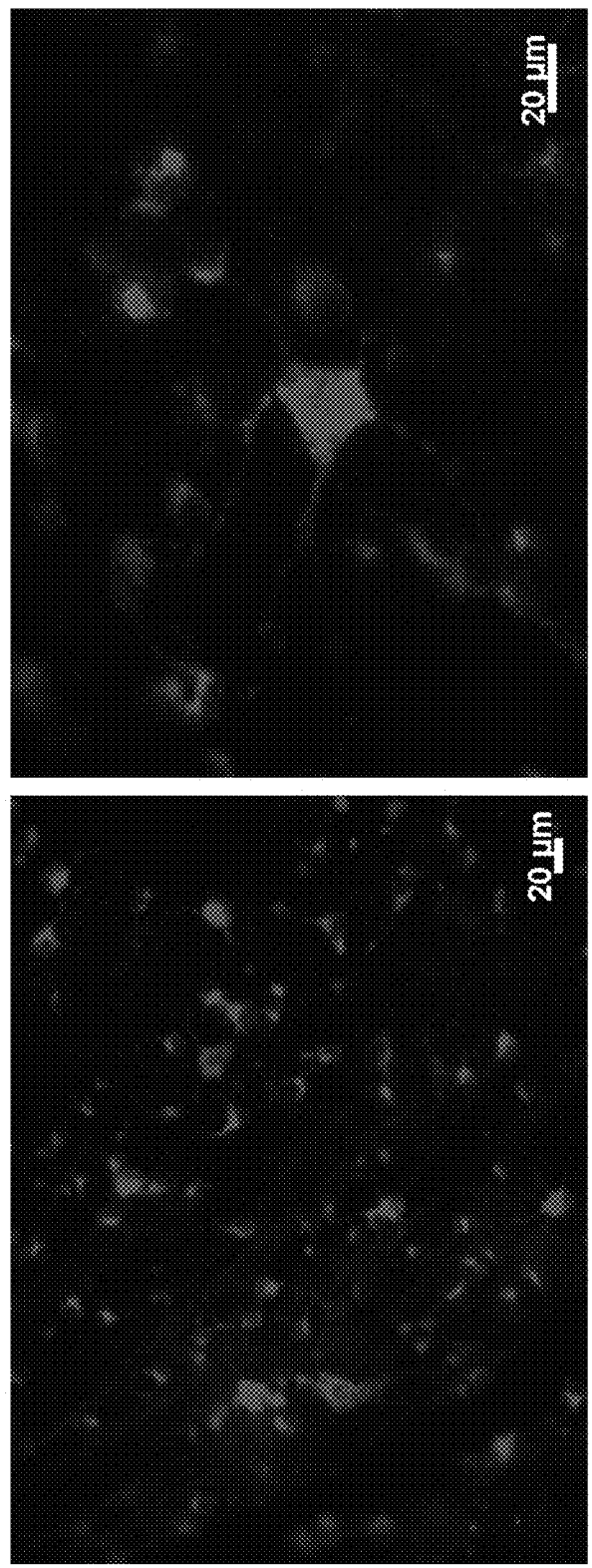
FIG. 5 is a pair of photographs of a flat-mounted retina preparation after ChR-HSB expression. In the figure, the left shows a low-magnification (×100) photograph, and the right shows a high-magnification (×200) photograph of the same site.

After virus injection, a flat-mounted retina preparation was prepared for the purpose of confirming the gene expression. The eye ball was fixed with a 4% paraform-aldehyde solution immediately after the removal thereof. After fixation, the anterior eye part was removed, and the nerve retina was peeled from the choroid. The nerve retina was flat-mounted on a slide glass, and the gene expression was confirmed under a fluorescence microscope (FIG. 5). FIG. 5 shows that the expression is observed throughout the retina.

Gene Introduction into HEK Cell

A plasmid vector containing hChR-YR, IRES2, and a puromycin resistance gene downstream of CAG promoter was produced and introduced into cultured HEK cells by an electroporation method. From 24 hours after introduction, the resultant cells were cultured in a 10% FBS-DMEM medium containing puromycin (1 μg/ml), and only transgenic cells were selected and subcultured. These cells were used in the following experiment.

Wavelength Sensitivity Measurement by Patch-Clamp Method

Apparatus used:
 Patch clamp amplifier: AXOPATCH200A
 A/D Converter: AXON DIGITALDATA1200
Solution in Electrode:
 120 mM CsOH
 100 mM glutamate
 50 mM HEPES
 2.5 mM MgCl
 2.5 mM MgATP
 5 mM $Na_2EGTA$
 1.2 mM leupeptin
 pH 7.4, adjusted by 1 N CsOH
Solution in Outside of Cell (Tyrode solution):
 138 mM NaCl
 3 mM KCl
 1 mM $CaCl_2$
 1 mM $MgCl_2$
 10 mM HEPES
 4 mM NaOH
 pH 7.4, adjusted by 1 N HCl The inward current following light stimulation was measured by a patch-clamp method. In the measurement, the membrane potential was clamped at −60 mV in a whole cell mode to measure the current flow through an ion channel. A xenon lamp was used for the light stimulation, and the light of each wavelength was obtained by using a filter.

Figure 6:
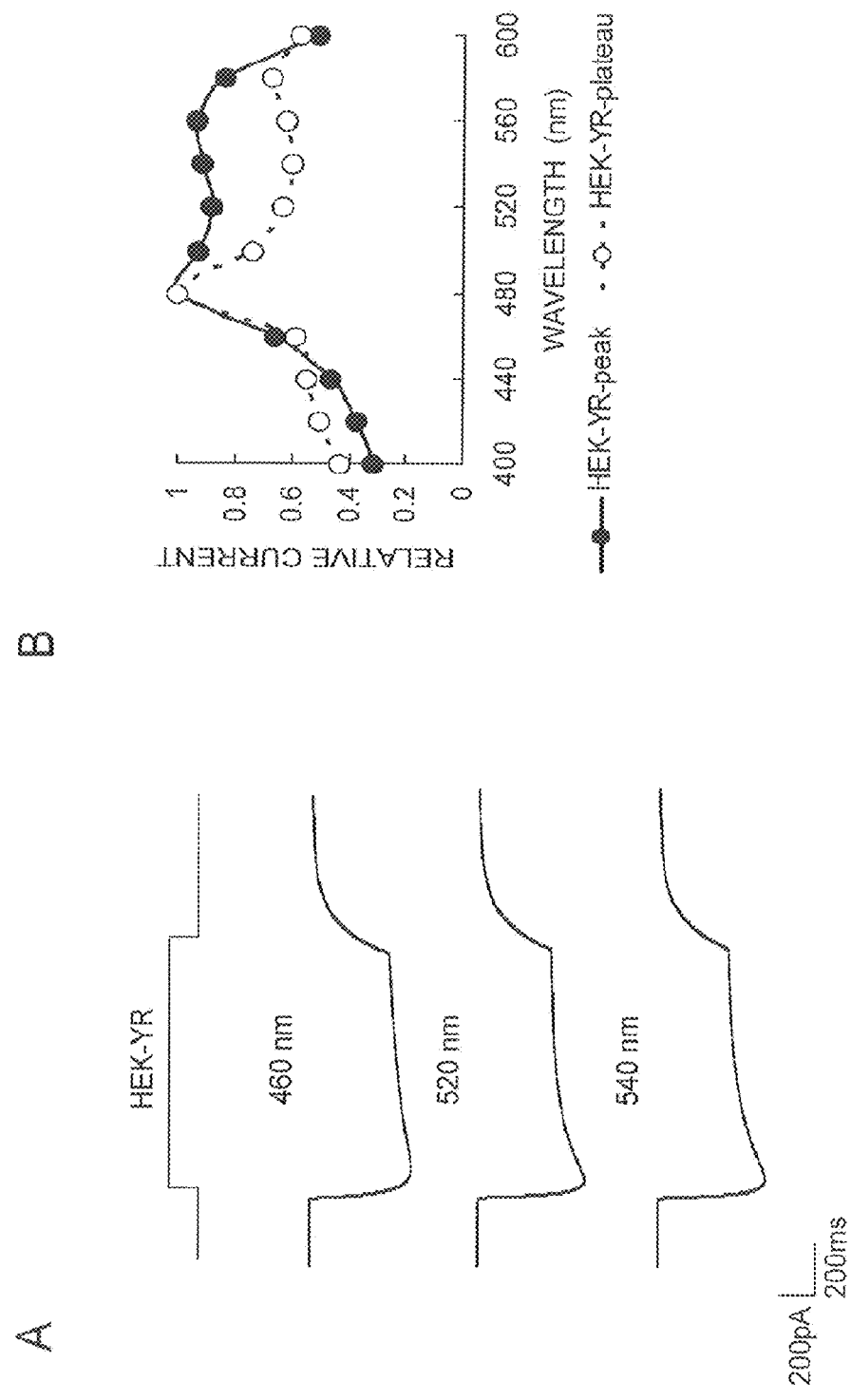
FIG. 6 is a pair of drawings showing results of measuring sensitivity to wavelength after introducing hChR-YR. Inward currents (left), and wavelength characteristics obtained by conversion from stimulus intensities of each wavelength from recorded inward currents (right).

The stimulus intensity of light of each wavelength is as follows.
 400 nm 0.021 mW
 420 nm 0.018 mW
 440 nm 0.027 mW
 460 nm 0.027 mW
 480 nm 0.018 mW
 500 nm 0.021 mW
 520 nm 0.015 mW
 540 nm 0.014 mW
 560 nm 0.012 mW The results are shown in FIG. 6. The inward current induced by the light stimulation of each wavelength was recorded (left) and a graph showing wavelength characteristics (right) was obtained by conversion from the stimulus intensity of each wavelength.

As a result, it was demonstrated that the cells after hChR-YR introduction had not only wavelength sensitivity toward red but also sensitivity to the blue range.

The results suggest the possibility that the introduction of one gene of hChR-YR into the lost retina could regenerate vision capable of seeing the whole range of visual light.

According to previous vision regeneration methods using ClChR2, wavelength sensitivity has been limited to a blue color; thus, it has been necessary to multiply introduce a similar gene having sensitivity to green or red (Si A, Cui J, Ma YP, et al. Ectopic expression of a microbial-type rhodopsin restores visual responses in mice with photoreceptor degeneration. *Neuron* 2006; 50: 23-33; Tomita H, Sugano E, Isago H, et al. Channelrhodopsin-2 gene transduced into retinal ganglion cells restores functional vision in genetically blind rats. *Exp. Eye Res.* 2010; 90: 429-436; Tomita H, Sugano E, Yawo H, et al. Restoration of visual response in aged dystrophic RCS rats using AAV-mediated channelopsin-2 gene transfer. *Invest. Ophthalmol. Vis. Sci.* 2007; 48: 3821-3826). Alternatively, for example, it has been thought that using an engineering technique employing a camera or the like, all images to be presented are converted to blue images, which are presented to the transgenic retina. However, the above results show that hChR-YR, having sensitivity to a wide range of wavelength, has been obtained, suggesting the possibility that single gene introduction enables the whole range of visual light to be seen.

As an application to other than vision, hChR-YR enables a body part deeper from the surface layer of tissue to be stimulated with light since hChR-YR has wavelength sensitivity toward red, having high permeability into tissue compared to a blue light.

Industrial Applicability

According to the present invention, a Volvox-derived light-receiving channel rhodopsin is provided which is improved in the expression efficiency on a cell membrane.

The light-receiving channel rhodopsin according to the present invention has sensitivity to yellow light to red light, preferably blue light to red light, and can be used, for example, for reconstructing mammalian visual function, because it shows efficient cell membrane-localized expression.

A channel rhodopsin is widely used as a tool for analyzing nerve function since the expression thereof in nerve cells enables the nerve cells to be artificially activated with light. Thus, the light-receiving channel rhodopsin of the present invention can probably be used as a useful tool in such research field.

All publications, Patents and Patent Applications cited herein are hereby incorporated as reference in their entirety.

The invention claimed is:

1. A modified Volvox carteri-derived light-receiving channel rhodopsin protein, wherein the protein is modified to comprise an N-terminal region of *Chlamydomonas reinhardtii*-derived channel rhodopsin-1 at the N-terminal of a Volvox carteri-derived light-receiving channel rhodopsin protein, wherein the N-terminal region imparts cell membrane-localized expression and comprises no transmembrane domain of the *Chlamydomonas reinhardtii*-derived channel rhodopsin-1, wherein the protein comprises (a) or (b) below:
   (a) the amino acid sequence shown in SEQ ID NO: 8 or SEQ ID NO: 10;
   (b) the amino acid sequence having at least 98% sequence identity to the amino acid sequence shown in SEQ ID NO:8 or SEQ ID NO: 10 and having biological activities equivalent to or higher than those of the polypeptides of (a), wherein the amino acid sequence comprises at least amino acids 1-66 of SEQ ID NO: 2.

2. The protein according to claim 1, wherein the protein further comprises a fluorescent protein at a C-terminal.

3. A polynucleotide encoding the protein according to claim 1.

4. An expression vector comprising the polynucleotide according to claim 3 functionally linked to a promoter.

5. A cell expressing the protein according to claim 1.

6. The cell according to claim 5, wherein the cell is a visual cell.

7. A method for treating a subject suffering from damage of the external layer of the retina, comprising;
   administering to said subject an effective amount of the protein according to claim 1, the polynucleotide of claim 3 or the expression vector of claim 4.

8. The method according to claim 7, wherein the damage of the external layer of the retina is retinal pigmentary degeneration, age-related macular degeneration, or retinal detachment.

9. A pharmaceutical composition for treating damage of the external layer of the retina, comprising;
   the protein according to claim 1, the polynucleotide according to claim 3, or the expression vector according to claim 4 as an active ingredient; and
   a pharmaceutically acceptable carrier.

10. The pharmaceutical composition according to claim 9, wherein the damage of the external layer of the retina is retinal pigmentary degeneration, age-related macular degeneration, or retinal detachment.

11. A method for preparing a protein, comprising;
    expressing said polynucleotide of claim 3 to prepare said protein.

12. The method of claim 11, wherein said polynucleotide is functionally linked to a promoter.

13. The modified Volvox carteri-derived light-receiving channel rhodopsin protein of claim 1, wherein the protein comprises (a) or (b) below:
    (a) the amino acid sequence shown in SEQ ID NO: 8;
    (b) an amino acid sequence having at least 98% sequence identity to the amino acid sequence shown in SEQ ID NO: 8 and having biological activities equivalent to or higher than those of the polypeptides of (a), wherein the amino acid sequence comprises at least amino acids 1-66 of SEQ ID NO: 2.

14. The modified Volvox carteri-derived light-receiving channel rhodopsin protein of claim 1, wherein the protein comprises (a) or (b) below:
    (a) the amino acid sequence shown in SEQ ID NO:10;
    (b) an amino acid sequence having at least 98% sequence identity to the amino acid sequence shown in SEQ ID NO: 10 and having biological activities equivalent to or higher than those of the polypeptides of (a), wherein the amino acid sequence comprises at least amino acids 1-66 of SEQ ID NO: 2.

15. The modified Volvox carteri-derived light-receiving channel rhodopsin protein of claim 1, wherein the protein comprises the amino acid sequence shown in SEQ ID NO:8.

16. The modified Volvox carteri-derived light-receiving channel rhodopsin protein of claim 1, wherein the protein comprises the amino acid sequence shown in SEQ ID NO:10.

* * * * *